United States Patent [19]
Maruyama et al.

[11] Patent Number: 5,939,403
[45] Date of Patent: Aug. 17, 1999

[54] KERATAN SULFATE OLIGOSACCHARIDE FRACTION AND PHARMACEUTICAL CONTAINING THE SAME

[75] Inventors: Hiroshi Maruyama, Akiruno; Kiyoshi Morikawa, Hinode-machi; Akira Tawada, Sayama; Satoshi Miyauchi, Musashimurayama; Keiichi Yoshida, Higashimurayama; Akira Asari, Iruma, all of Japan

[73] Assignee: Seikagaku Corporation, Tokyo, Japan

[21] Appl. No.: 08/849,925

[22] PCT Filed: Nov. 22, 1995

[86] PCT No.: PCT/JP95/02386

§ 371 Date: Jun. 2, 1997

§ 102(e) Date: Jun. 2, 1997

[87] PCT Pub. No.: WO96/16973

PCT Pub. Date: Jun. 6, 1996

[30] Foreign Application Priority Data

Dec. 1, 1994 [JP] Japan ..................... 6-298298

[51] Int. Cl.$^6$ ........... A61K 31/73; A61K 31/725; C08B 3/04; C08B 3/06
[52] U.S. Cl. ............... 514/53; 514/54; 514/61; 536/123; 536/123.1; 536/123.13
[58] Field of Search ................. 514/54, 61, 62, 514/53; 536/29.1, 123.1, 123.13; 435/200

[56] References Cited

U.S. PATENT DOCUMENTS

| | | | |
|---|---|---|---|
| 4,665,060 | 5/1987 | Mardh et al. | 514/61 |
| 4,851,338 | 7/1989 | Mardh et al. | 435/34 |
| 5,489,578 | 2/1996 | Rosen et al. | 514/61 |
| 5,514,660 | 5/1996 | Zopf et al. | 514/25 |
| 5,580,862 | 12/1996 | Rosen et al. | 514/61 |

FOREIGN PATENT DOCUMENTS

| | | |
|---|---|---|
| 240098 | 10/1987 | European Pat. Off. . |
| 269937 | 6/1988 | European Pat. Off. . |
| 0 361 490 A2 | 4/1990 | European Pat. Off. . |
| 0 798 376 A1 | 10/1997 | European Pat. Off. . |
| 04135496 | 5/1992 | Japan . |
| WO 91/06303 | 5/1991 | WIPO . |
| WO/93/24506 | 12/1993 | WIPO . |
| WO/95/21618 | 8/1995 | WIPO . |

OTHER PUBLICATIONS

Brown et al. *Eur. J. Biochem,* vol. 224(2):281–308 Abstract Only, 1994.
Brown et al. *Biochemistry,* vol. 33(16):4836–4846 Abstract Only, 1994.
Kobayashi, Masanori: Yamazaki, Fumito: Ito, Yukishige: Ogawa, Tomoya: A Synthetic Approach to Keratan Sulfate: I. Synthesis of Trisulfated glycoteraose, *Tetrahedron Letters,* vol. 30, No. 34, pp. 4547–4550, 1989.
"The Carbhydrates, Chemistry and Biochemistry" Second Edition, 1970, vol. 11B, Academic Press, editors Ward Pigman, Derek Horton and Anthony Herp.

*Primary Examiner*—Howard C. Lee
*Attorney, Agent, or Firm*—Knobbe, Martens Olson & Bear, LLP

[57] ABSTRACT

A keratan sulfate oligosaccharide which comprises from two to five sugar units and has sulfated N-acetylglucosamine at the reducing end and in a molecule of which at least two hydroxyl groups are sulfated, preferably, which contains at least disaccharide represented by the formula Gal(6S)-GlcNAc(6S) (in the formula, Gal, GlcN, Ac, and 6S represent a galactose, a glucosamine, an acetyl group, and a 6-O-sulfate ester, respectively) as a constitutional ingredient, and/or pharmaceutically acceptable salt thereof are used as active ingredients of anti-inflammatory agents, antiallergic agents, immunomodulators, cell differentiation inducers, and apoptosis inducers.

9 Claims, 19 Drawing Sheets

KERATAN SULFATE OLIGOSACCHARIDE FRACTION AND PHARMACEUTICAL CONTAINING THE SAME

This application is a 371 of PCT/JP 95/02386 filed on Nov. 22, 1995.

TECHNICAL FIELD

The present invention relates to an anti-inflammatory agent, antiallergic agent, immunomodulator, cell differentiation inducer, apoptosis inducer, and a keratan sulfate oligosaccharide which is useful as an active ingredient of these pharmaceuticals.

BACKGROUND ART

Keratan sulfate is a glycosaminoglycan having N-acetyllactosamine as the basic structure which has O-sulfated hydroxyl group at C-6 position of the N-acetylglucosamine residue. Especially, high-sulfated keratan sulfate which further has a sulfated hydroxyl group beside that at C-6 position of N-acetylglucosamine residue in the constitutional disaccharide unit is known to be contained in cartilaginous fishes such as sharks, and cartilage, bone and cornea of mammals such as whale and bovines. As a method for producing a keratan sulfate oligosaccharide which is the degradation product of the keratan sulfate, a method which comprises allowing a keratan sulfate degrading enzyme (keratanase II; Japanese Patent Application Laid-open No. 2-57182) derived from the microorganism belonging to the genus Bacillus to act on keratan sulfate has been reported.

Further, there is a report (Biochemistry, 33, 4836–4846 (1994)) which analyzes 25 kinds of the oligosaccharide fractions obtained by the fractionation of degradation products after degrading keratan sulfate derived from bovine cartilage with keratanase II and infers the structures of the tetrasulfated N-acetyllactosamine tetrasaccharide represented by the following formula (I) (hereinafter also referred to as "keratan sulfate tetrasaccharide (I)"), the trisulfated N-acetyllactosamine pentasaccharide represented by the following formula (II) (hereinafter also referred to as "keratan sulfate pentasaccharide (II)"), the disulfated N-acetyllactosamine disaccharide represented by the following formula (III) (hereinafter also referred to as "keratan sulfate disaccharide (III)"), and the like.

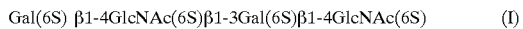

Gal(6S) β1-4GlcNAc(6S)β1-3Gal(6S)β1-4GlcNAc(6S)  (I)

NeuAc~Galβ1-4GlcNAc(6S)β1-3Gal(6S)β1-4GlcNAc(6S)  (II)

Gal(6S)β1-4GlcNAc(6S)  (III)

(In the foregoing formulae, Gal represents a galactose, GlcN represents a glucosamine, Neu represents a neuraminic acid, Ac represents an acetyl group, and 6S represents a 6-O-sulfate ester. And "~" represents an α2,3 bond or α2,6 bond.)

Up to now, however, no reports have appeared concerning efficient mass production of pure keratan sulfate oligosaccharide, especially the keratan sulfate tetrasaccharide (I), the keratan sulfate pentasaccharide (II), and the keratan sulfate disaccharide (III), without contamination of impurities (for example, endotoxin, nucleic acid, protein, protease, other glycosaminoglycans except for keratan sulfate oligosaccharide, and the like). The contamination of such impurities is liable to be a serious defect especially in the case where the keratan sulfate oligosaccharide is used as pharmaceuticals. Furthermore, the pharmacological functions (especially anti-inflammatory function, antiallergic function, immunomodulating function, cell differentiation inducing function, and apoptosis inducing function) of the keratan sulfate oligosaccharide are not known at all.

DISCLOSURE OF THE INVENTION

The present invention has been acomplished from the viewpoint as described above, an object of which is to provide a use of keratan sulfate oligosaccharide without substantial contamination of impurities as anti-inflammatory agents, antiallergic agents, immunomodulators, cell differentiation inducers (hereinafter also reffered to as "differentiation inducers"), or apoptosis inducers.

In order to achieve the above object, the present inventors made an diligent studies on the pharmacological functions of the oligosaccharide which comprises from two to five sugar units, especially disaccharide, tetrasaccharide or pentasaccharide prepared from degradation products which are obtained by degrading high-sulfated keratan sulfate with a keratan sulfate degrading enzyme, and as a result, it has been found that the oligosaccharide described above and the salt thereof have an excellent anti-inflammatory function, anti-allergic function, immunomodulating function, cell differentiation inducing function, and apoptosis inducing function. Thus, the present invention has been completed.

Namely, the anti-inflammatory agent, antiallergic agent, immunomodulator, differentiation inducer, and apoptosis inducer of the present invention (hereinafter also generically referred to as "the pharmaceuticals of the present invention") comprise keratan sulfate oligosaccharide and/or the pharmaceutically acceptable salt thereof as an active ingredient. In this specification, "the keratan sulfate oligosaccharide" means the degradation product of keratan sulfate which can be obtained by degrading keratan sulfate with a keratan sulfate degrading enzyme of endo-β-N-acetylglucosaminidase type.

The keratan sulfate oligosaccharide used for the pharmaceuticals of the present invention is exemplified by the keratan sulfate oligosaccharide which comprises a sulfated N-acetyllactosamine unit optionally containing sialic acid and/or fucose, the keratan sulfate oligosaccharide which comprises oligosaccharide having from two to five sugar units and having sulfated N-acetylglucosamine at a reducing end thereof, and in a molecule of which at least two hydroxyl groups are sulfated, and especially the keratan sulfate oligosaccharide described above which contains at least the disaccharide represented by the formula Gal(6S)-GlcNAc(6S) (wherein Gal represents a galactose, GlcN represents a glucosamine, Ac represents an acetyl group, and 6S represents a 6-O-sulfate ester) as a constitutional ingredient. Moreover, a preferable example of the keratan sulfate oligosaccharide described above includes the tetrasulfated N-acetyllactosamine tetrasaccharide represented by the following formula (I), the trisulfated N-acetyllactosamine pentasaccharide represented by the formula (II), the disulfated N-acetyllactosamine disaccharide represented by the formula (III), and the like.

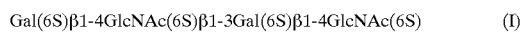

Gal(6S)β1-4GlcNAc(6S)β1-3Gal(6S)β1-4GlcNAc(6S)  (I)

NeuAc~Galβ1-4GlcNAc(6S)β1-3Gal(6S)β1-4GlcNAc(6S)  (II)

Gal(6S)β1-4GlcNAc(6S)  (III)

(In the formulae, Gal represents a galactose, GlcN represents a glucosamine, Neu represents a neuraminic acid, Ac represents an acetyl group, and 6S represents a 6-O-sulfate ester. And ~ represents an α2,3 bond or α2,6 bond.)

The present invention also provides a keratan sulfate oligosaccharide fraction containing not less than 99% of keratan sulfate oligosaccharide which comprises oligosaccharide having from two to five sugar units and having sulfated N-acetylglucosamine at a reducing end thereof, in a molecule of which at least two hydroxyl groups are sulfated, and having the following properties:

(a) the fraction does not substantially contain endotoxin, and contents of nucleic acid, protein and protease in the fraction are respectively less than detection limits thereof; and (b) the fraction does not substantially contain hyaluronic acid, chondroitin sulfate, dermatan sulfate, heparan sulfate, and keratan sulfate.

The present invention also provides a keratan sulfate oligosaccharide fraction containing not less than 99% of keratan sulfate oligosaccharide which contains at least disaccharide represented by the formula Gal(6S)-GlcNAc(6S) as a constitutional ingredient, and having the properties (a) and (b) described above. Further, a preferable example of the keratan sulfate oligosaccharide contained in the oligosaccharide fractions described above includes the tetrasulfated N-acetyllactosamine tetrasaccharide represented by the formula (I) described above, the trisulfated N-acetyllactosamine pentasaccharide represented by the formula (II), the disulfated N-acetyllactosamine disaccharide represented by the formula (III), and the like. Furthermore, the keratan sulfate oligosaccharide includes that obtained by fractionating degradation products, after degrading high-sulfated keratan sulfate derived from cartilaginous fishes with a keratan sulfate degrading enzyme of endo-β-N-acetylglucosaminidase type.

Moreover, the present invention provides a method for producing a keratan sulfate oligosaccharide fraction comprising the steps of degrading keratan sulfate with a keratan sulfate degrading enzyme having the following physical and chemical properties:

(1) action:
the degrading enzyme acts on keratan sulfate and hydrolyzes the N-acetylglucosaminidic linkage thereof;

(2) substrate specificity:
the degrading enzyme acts on keratan sulfate I, keratan sulfate II, and keratan polysulfate and produces sulfated keratan sulfate disaccharide and sulfated keratan sulfate tetrasaccharide as main degradation products; and, preferably, further having the following physical and chemical properties;

(3) optimum reaction pH:
the degrading enzyme has an optimum reaction pH of from 4.5 to 6 in the 0.1 M acetate buffer or 10 mM tris-acetate buffer at 37° C.;

(4) pH stability:
the degrading enzyme has a pH stability of from 6 to 7 when the degrading enzyme is stood in the 0.1 M acetate buffer or 10 mM tris-acetate buffer at 37° C. for an hour;

(5) optimum reaction temperature:
the degrading enzyme has an optimum reaction temperature of from 50 to 60° C. when the degrading enzyme reacts in the 0.1 M acetate buffer, pH 6.0, for 10 minutes; and (6) thermostability:
the degrading enzyme is at least stable at 45° C. or less when the degrading enzyme is stood in the 0.1 M acetate buffer, pH 6.0, for an hour; and fractionating a keratan sulfate oligosaccharide fraction having the following properties from the degradation products:

(A) the fraction contains as a main ingredient, the keratan sulfate oligosaccharide which has sulfated N-acetyllactosamine as the basic constitutional structure;

(B) the fraction does not substantially contain endotoxin, and contents of nucleic acid, protein and protease in the fraction are respectively trace or less than detection limits thereof; and (C) the fraction does not substantially contain hyaluronic acid, chondroitin sulfate, dermatan sulfate, heparan sulfate, and keratan sulfate.

Further, in the method for producing the keratan sulfate oligosaccharide fraction described above, for instance, the use of high-sulfated keratan sulfate as the material keratan sulfate yields the keratan sulfate oligosaccharide containing the tetrasulfated N-acetyllactosamine tetrasaccharide represented by the formula (I) described above, the trisulfated N-acetyllactosamine pentasaccharide represented by the formula (II), the disulfated N-acetyllactosamine disaccharide represented by the formula (III), and the like, especially the keratan sulfate oligosaccharide containing the tetrasulfated N-acetyllactosamine tetrasaccharide represented by the formula (I) and the disulfated N-acetyllactosamine disaccharide represented by the formula (III) as main ingredients.

In the present invention, preferable keratan sulfate oligosaccharide which comprises oligosaccharide having from two to five sugar units is normally that of which from two to four sites are sulfated. Further in the keratan sulfate oligosaccharide containing sialic acid which can be used in the present invention, the sialic acid includes N-acetylneuraminic acid and N-glycolylneuraminic acid, and N-acetylneuraminic acid is preferable. The keratan sulfate oligosaccharide which can be used in the present invention described above includes those binding sialic acid by the α2,3 bond and α2,6 bond, and that binding sialic acid by the α2,3 bond is preferable.

The present invention will be illustrated in detail below.

(1) Keratan sulfate oligosaccharide and keratan sulfate oligosaccharide fraction used in the present invention The keratan sulfate which is the starting material of keratan sulfate oligosaccharide used in the present invention mainly comprises the repeating structure of the disaccharide of galactose or galactose-6-sulfate and N-acetylglucosamine-6-sulfate, the sulfate content of which varies depending upon animal species, tissue, etc., and is normally produced from the raw materials such as cartilage, bone and cornea of cartilaginous fishes such as sharks and mammals such as whale and bovines.

The keratan sulfate used as the material is generally available one and not especially limited, but preferably high-sulfated keratan sulfate (the high-sulfated keratan sulfate containing from 1.5 to 2 molecules of the sulfate group per a constitutional disaccharide is also referred to as keratan polysulfate) of which the constitutional sugar as the galactose residue is sulfated. The sulfate group is preferably situated at C-6 position on the galactose residue. Such high-sulfated keratan sulfate can be obtained from, for example, proteoglycan of the cartilage of cartilaginous fishes such as sharks. And also, the commercially available one can be used.

The keratan sulfate oligosaccharide of the present invention can be obtained by allowing a keratan sulfate degrading enzyme of endo-β-N-acetylglucosaminidase type, for example keratanase II derived from the microorganism belonging to the genus Bacillus (Japanese Patent Application Laid-open No. 2-57182), or a novel keratan sulfate degrading enzyme found from a microorganism belonging to the genus Bacillus by the present inventors to act on keratan sulfate, preferably high-sulfated keratan sulfate in buffered solution to degrade, and then fractionating the degradation products obtained. This degradation reaction is, for example, carried out by allowing a buffered solution containing keratan sulfate in concentration from 1.0 to 100 mg/ml which is adjusted to pH from 6.0 to 7.0 to react at from 25 to 40° C. for from 1 to 72 hours. In this reaction, the concentration of the buffer is normally in the range from 0.01 to 0.2 M. The kinds of the buffer is not limited especially as far as the pH of which may be adjusted to the range described above, and includes, for example, acetate buffer, phosphate buffer, and tris buffer. The quantity of the enzyme used in the degradation reaction is, for example, in the range from 0.1 to 1.0 unit for 1 g of keratan sulfate. Herein, the one unit means the quantity of the enzyme which produces reducing end corresponding to 1 pmol of N-acetylglucosamine in a minute.

The novel keratan sulfate degrading enzyme described above is produced by a microorganism belonging to *Bacillus circulans*, for example *Bacillus circulans* KsT202 has been separated by the present inventors, and has an excellent thermostability. This enzyme is obtained by culturing *Bascillus circulans* KsT202 in a suitable medium, and purifying the enzyme from the medium and/or the microbial cells by the conventional methods for the general enzyme purification. The *Bascillus circulans* KsT202 had been deposited in National Institute of Bioscience and Human-Technology of Agency of Industrial Science and Technology of Ministry of International Trade and Industry (1-3, Higashi 1-chome, Tsukuba-shi, Ibaraki-ken 305, Japan) on Sep. 5, 1994 under accession number FERM P-14516, and then it was transferred to the international deposition based on Budapest treaty on Nov. 6, 1995 and has been deposited under accession number FERM BP-5285.

Physical and chemical properties of the novel keratan sulfate degrading enzyme described above will hereinafter be illustrated. (1) Action:

The degrading enzyme acts on keratan sulfate and hydrolyzes the N-acetylglucosaminidic linkage thereof.

(2) Substrate specificity:

The degrading enzyme acts on keratan sulfate I, keratan sulfate II, and keratan polysulfate and produces sulfated keratan sulfate disaccharide and sulfated keratan sulfate tetrasaccharide as the main degradation products. Also it is confirmed that the degrading enzyme produces sulfated keratan sulfate pentasaccharide.

(3) Optimum reaction pH:

The degrading enzyme has an optimum reaction pH of from 4.5 to 6 in the 0.1 M acetate buffer or 10 mM tris-acetate buffer at 37° C.

(4) pH Stability:

The degrading enzyme has a pH stability of from 6 to 7 when the degrading enzyme is stood in the 0.1 M acetate buffer or 10 mM tris-acetate buffer at 37° C. for an hour.

(5) Optimum reaction temperature:

The degrading enzyme has an optimum reaction temperature of from 50 to 60° C. when the degrading enzyme reacts in the 0.1 M acetate buffer, pH 6.0, for 10 minutes.

(6) Thermostability:

The degrading enzyme is at least stable at 45° C. or less when the degrading enzyme is stood in the 0.1 M acetate buffer, pH 6.0, for an hour.

The keratan sulfate oligosaccharide fraction of the present invention can be produced further by the reaction using the immobilized enzyme of keratan sulfate degrading enzyme including such novel keratan sulfate degrading enzyme and keratanase II described above, which is immobilized by the conventional methods.

Owing to the degradation reaction by such enzyme described above, keratan sulfate is degraded into oligosaccharide.

Then the oligosaccharide obtained above is separated and purified by conventional methods such as ethanol precipitation and varieties of chromatography, and the desired keratan sulfate oligosaccharide can be yielded. This purification will be illustated in detail by describing the purification of keratan sulfate oligosaccharide of disaccharide, tetrasaccharide and pentasaccharide. The degradation product described above is usually concentrated by ethanol precipitation first and gel filtration (fractionated molecular weight range: 100 to 10,000) to roughly fractionate into crude keratan sulfate oligosaccharide of disaccharide, tetrasaccharide and pentasaccharide. Then the crude fractions were separated and fractionated by anion exchange chromatography, respectively, to give substantially pure disaccharide, tetrasaccharide and pentasaccharide, which do not substantially contain endotoxin, contents of nucleic acid, protein and protease in which are less than detection limits thereof, and which do not substantially contain hyaluronic acid, chondroitin sulfate, dermatan sulfate, heparan sulfate, and keratan sulfate. In this invention, "not substantially contain" means containing to the extent that the content may be detected by sensitive detection methods but does not influence the pharmacological functions of keratan sulfate oligosaccharide such as anti-inflammatory function, anti-allergic function, immunomodulating function, cell differentiation inducing function, and apoptosis inducing function.

The keratan sulfate oligosaccharide of the present invention is obtained from the keratan sulfate as material by degrading the keratan sulfate with endo-β-N-acetylglucosaminidase and fractionating oligosaccharide of from disaccharide to pentasaccharide unit, and does not substantially contain keratan sulfate, which is the material thereof.

The keratan sulfate oligosaccharide can be also obtained from the degradation products of the keratan sulfate degraded by the chemical degradation method which preferentially or specifically degrades the N-acetylglucosaminidic linkage between galactose or galactose-6-sulfate and N-acetylglucosamine-6-sulfate, which constitutes keratan sulfate.

The keratan sulfate oligosaccharide, especially the tetrasulfated N-acetyllactosamine tetrasaccharide represented by the formula (I) described above, the trisulfated N-acetyllactosamine pentasaccharide represented by the formula (II), the disulfated N-acetyllactosamine disaccharide represented by the formula (III), and the like, is obtained as described above. In examples described afterwards, the nuclear magnetic resonance spectra ($^1$H-NMR and $^{13}$C-NMR) and the result of fast atomic bombardment mass spectrometry analysis of the substances represented by the formula (I), (II) and (III) will be shown.

And the keratan sulfate oligosaccharide used in the present invention also includes the ionized body, proton-added body, and pharmaceutically acceptable salt among the salts with inorganic bases such as alkaline metals (sodium, potassium, lithium, etc.), alkali earth metals (calcium etc.), ammonium, and the like, or the salts with organic bases such as diethanolamine salt, cyclohexylamine salt, and amino acid salt.

The pharmaceutical composition comprising the keratan sulfate oligosaccharide and/or the salt thereof used in the present invention, and carriers, vehicles, and other additives usually used in pharmaceuticals is also novel and can be administered with the object of anti-inflammation, antiallergy, immunomodulating, cell differentiation inducing, apoptosis inducing, and the like.

The keratan sulfate oligosaccharide fraction of the present invention contains at least 99% of keratan sulfate oligosaccharide, which is obtained by removing endotoxin, nucleic acid, protein, protease, and other glycosaminoglycans except for the desired keratan sulfate oligosaccharide from the enzymatic degradation products of keratan sulfate, especially the enzymatic degradation products of high-sulfated keratan sulfate, following the method described above.

(2) Pharmaceutical of the present invention

The keratan sulfate oligosaccharide and/or the pharmaceutically acceptable salt thereof described above may be widely used as anti-inflammatory agent, antiallergic agent, immunomodulator, cell differentiation inducer, apoptosis inducer, and the pharmaceuticals for other use.

The anti-inflammatory agent of the present invention is effective for any disease so far concerned with inflammation, and the specific indication of which includes chronic rheumatoid arthritis, systemic lupus erythematodes, spondylitis deformans, osteoarthritis, lumbago, remission of inflammation and enlargement after operations and traumas, scapula periarthritis, temporomandibular arthrosis, tendovaginitis, tendon ambient inflammation, inflammation of condyle of humerus (tennis elbow), myalgia, keratoconjunctivitis, and the like. The anti-inflammatory agent of the present invention has anti-inflammatory functions such as an analgesic function, an antiphlogistic function, and an antipyretic function upon these diseases and symptoms actioned by the contained keratan sulfate oligosaccharide and/or the pharmaceutically acceptable salt thereof.

The antiallergic agent of the present invention is effective for any disease so far concerned with allergy, and the specific indication of which includes allergic rhinitis, allergic keratoconjunctivitis, vernal conjunctivitis, eczema, dermatitis, urticaria, atopic dermatitis, and the like.

The immunomodulator of the present invention is effective for any disease so far caused by immune abnormality, and the specific indication of which includes human autoimmune lymphoproliferative syndrome (Cell 81, 935–946 (1995), Science 268, 1347–1349 (1995)), lymphoproliferative disorder (Leukemia and Lymphoma 16, 363–368 (1995)), angioimmunoblastic lymphadenopathy (Blood 85(10), 2862–2869 (1995)), immunoblastic lymphadenopathy (The American Journal of Medicine 63, 849- (1977)), chronic rheumatoid arthritis, systemic lupus erythematodes, discoid lupus erythematodes, multiple myositis (dermatomyoma), scleroderma, mixed connective-tissue disease, chronic thyroiditis, primary myxedema, thyrotoxicosis, pernicious anemia, Good-pasture syndrome, acute progressive glomerulonephritis, myasthenia gravis, pemphigus vulgaris, bullous pemphigoid, non-insulin dependent diabetes mellitus, juvenile diabetes mellitus, Addison's disease, atrophic gastritis, male sterility, climacteric precox, phacogenic uveitis, sympathetic angitis, multiple sclerosis, progressive systemic sclerosis, inflammatory intestinal disease (Crohn's disease, ulcerative colitis, etc.), primary biliary cirrhosis, chronic active hepatitis, autoimmune hemolytic anemia, paroxysmal hemoglobinuria, idiopathic thrombocytopenic purpura, Sjögren's syndrome, antiphospholipid antibody syndrome, and the like.

The differentiation inducer of the present invention is effective for any disease so far caused by failure of physiological cell differentiation, immune abnormality, malignant tumor, etc., and the specific indication of which includes human autoimmune lymphoproliferative syndrome, lymphoproliferative disorder, angioimmunoblastic lymphadenopathy, immunoblastic lymphadenopathy, chronic rheumatoid arthritis, systemic lupus erythematodes, inflammatory intestinal disease (Crohn's disease, ulcerative colitis, etc.), progressive systemic sclerosis, multiple myositis (dermatomyoma), Sjögren's syndrome, carcinoma, leukemia, lymphoma, carcinoma metastasis inhibition, hyperplasia prevention (treatment for psoriasis etc.), wound healing, osteomyelodysplasia syndrome, scleroderma, and the like.

The apoptosis inducer of the present invention is effective for any disease so far caused by failure of physiological apoptosis, immune abnormality, malignant tumor, etc., and the specific indication of which includes human autoimmune lymphoproliferative syndrome, lymphoproliferative disorder, angioimmunoblastic lymphadenopathy, immunoblastic lymphadenopathy, chronic rheumatism, systemic lupus erythematodes, ulcerative colitis, progressive systemic sclerosis, multiple myositis (dermatomyoma), Sjögren's syndrome, carcinoma, leukemia, lymphoma, carcinoma metastasis inhibition, hyperplasia prevention (treatment for psoriasis etc.), osteomyelodysplasia syndrome, scleroderma, apoptosis inducing of abnormal mesangial cells (treatment for glomerulonephritis), and the like.

In MRL-lpr/lpr mouse, the effects of depression of lymph node weight, differentiation inducing, and apoptosis inducing were observed. The pathogenesis of human autoimmune lymphoproliferative syndrome is considered the abnormality of Fas gene in the same manner as the MRL-lpr/lpr mouse, and the pathology of the syndrome has a marked resemblance to that of the MRL-lpr/lpr mouse such as from the oncoides of lymph node. The MRL-lpr/lpr mouse can be accepted as an appropriate model of human autoimmune lymphoproliferative syndrome. Therefore, the most preferable indication of the pharmaceuticals in the immunomodulator, the differentiation inducer, and the apoptosis inducer of the present invention is human autoimmune lymphoproliferative syndrome.

The pharmaceuticals of the present invention can be pharmaceutically manufactured according to the administration method such as injection (intramuscular, subcutaneous, intradermal, intravenous, intra-articular, intraocular, intraperitoneal, etc.), eye dropping, instillation, transcutaneous administration, oral administration, and inhalation. The dosage form includes injections (solutions, suspensions, emulsions, solid injections dissolved in use, etc.), tablets, capsules, granules, powders, solutions, liposome inclusions, ointments, gels, external powders, sprays, inhalation powders, eye drops, eye ointments, and so on. In the manufacture of pharmaceuticals, the ingredients usually used in drug products such as conventional vehicles, binders, lubricants, other colorants, and disintegrants can be used. And, in the pharmaceuticals of the present invention, keratan sulfate oligosaccharide can be simultaneously used with other anti-inflammatory ingredients, antiallergic ingredients, immunomodulating ingredients, differentiation inducing ingredients, apoptosis inducing ingredients, etc.

Table 1 shows the preferable administration methods and dosage forms in the anti-inflammatory agent and antiallergic agent. And Table 2 shows those in the immunomodulator, cell differentiation inducer, and apoptosis Inducer.

TABLE 1

| Administration Route | Dosage Form |
| --- | --- |
| Intravenous, Intramuscular, Subcutaneous, Intradermal, Intra-articular, and Intraocular Administration | Injections |
| Eye Dropping | Eye Drops |
| Instillation | Ointments |
| Oral Administration | Tablets, Capsules, Granules, Powders, Solutions, and Liposome Inclusions |
| Transcutaneous Administration | Ointments, Gels, External Powders, and Sprays |
| Inhalation | Sprays and Inhalation Powders |

TABLE 2

| Administration Route | Dosage Form |
| --- | --- |
| Intravenous, Intramuscular, Subcutaneous, and Intradermal Administration | Injections |
| Oral Administration | Tablets, Capsules, Granules, Powders, Solutions, and Liposome Inclusions |

The effective dose estimate of the anti-inflammatory agent and antiallergic agent of the present invention ranges from 30 to 300 mg/person/day of the keratan sulfate oligosaccharide in systemic administration and from 1 to 10 mg/person/day in topical administration. And that of the immunomodulator, differentiation inducer, and apoptosis inducer ranges from 30 to 6,000 mg/person/day of the keratan sulfate oligosaccharide.

PREFERRED EMBODIMENTS FOR CARRYING OUT THE INVENTION

Figure 1:
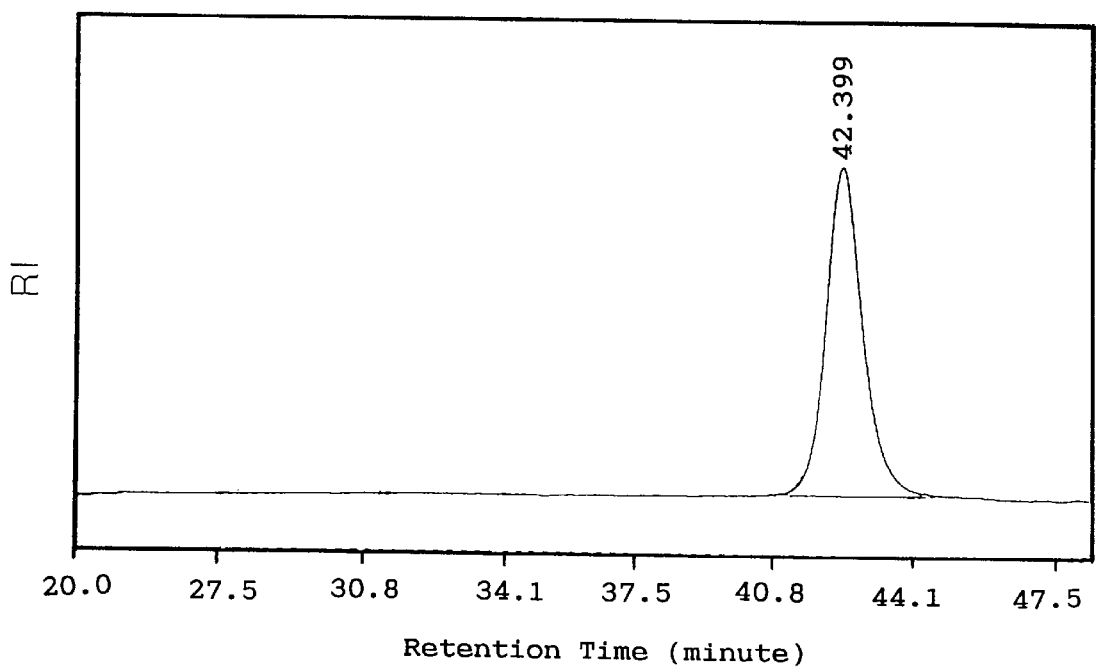
FIG. 1 shows the chromatogram in gel filtration by HPLC of the tetrasulfated N-acetyllactosamine tetrasaccharide (keratan sulfate tetrasaccharide (I)) produced in Example 1.

The present invention will be described more specifically with reference to the following examples. The production example will describe the production example of a novel keratan sulfate degrading enzyme obtained from a microorganism belonging to the genus Bacillus. Example 1 describes the production example of a keratan sulfate oligosaccharide fraction, and Example 2 describes example of acute toxicity and varieties of pharmacological properties of the keratan sulfate oligosaccharide. Further, Examples 3–6 will exemplify the pharmaceuticals.

PRODUCTION EXAMPLE: Production of Keratan Sulfate
Degrading Enzyme (1) Isolation of *Bascillus circulans* KsT202

A small amount of the soil was added to 5 ml of a liquid medium containing a nitrogen source, inorganic salts, and keratan sulfate, and cultured with shaking at 45° C. for three days. After the cultivation, 10 μl of the supernatant of the cultured medium was spotted on a filter paper, and 10 μl of the liquid medium (control) was also spotted on the filter paper in the same way. After air-drying, the filter paper was soaked in a toluidine blue solution and washed adequately with a dilute acetic acid solution, and the color on the spotted site of the supernatant of the culture medium was compared with that of the control. Since toluidine blue combines with keratan sulfate to develop a blue color, it was confirmed that a keratan sulfate assimilative microorganism existed in the sample developing a less color than the control. The keratan sulfate assimilative microorganism was pure-isolated by a conventional method from the culture solution using a plate medium (e.g., Heart infusion Agar).

Throug a variety of the microorganism pure-isolated were examined for the assimilation of keratan sulfate using a liquid medium in the same manner as described above, the desired keratan sulfate assimilative microorganism was obtained. As the result of the investigation of the morphological, growth, and physiological properties of the present strain, the microorganism has been identified as *Bacillus circulans*. The present strain is a novel one which can be distinguished from the known ones since it assimilates keratan sulfate. The *Bascillus circulans* KsT202 had been deposited in National Institute of Bioscience and Human-technology of Agency of Industrial Science and Technology on Sep. 5, 1994 under accession number FERM P-14516, and then it was transferred to the international deposition based on Budapest treaty on Nov. 6, 1995, and has been deposited under accession number FERM BP-5285.

(2) Preparation of keratan sulfate degrading enzyme

20 L of a medium (pH 8.0) containing 1.5% of peptone (Kyokuto Seiyaku Kogyo), 0.75% of beer yeast extract (Nippon Seiyaku), 0.75% of keratan polysulfate prepared from cartilage of sharks (Seikagaku Corporation), 0.5% of $K_2HPO_4$, 0.02% of $MgSO_4 \cdot 7H_2O$, 0.5% of NaCl, and 0.0015% of an antiforming agent, Adekanol LG109 (trade name, Asahi Denka Kogyo) was put into a jar fermenter with a capacity of 30-L, autoclaved at 121° C. for 20 minutes, inoculated aseptically with 1 L (5%) of the cultured solution of the strain KsT202 which was previously cultured with shaking in the same medium at 37° for 16 hours, and cultured at 45° C. for 24 hours with aeration (1 vvm) and agitation (300 rpm). 20 L of the cultured solution was treated with a continuous centrifuge to remove the microbial cells and give approximately 20 L of the extracellular fluid.

To this extracellular fluid, ammonium sulfate was added to 70% saturation, and the deposited precipitate was recovered by centrifugation and dissolved in 2.5 L of the 10 mM tris-acetate buffer (pH 7.5). To this solution, ammonium sulfate was added to 35% saturation, the deposited precipitate was removed by centrifugation, further ammonium sulfate was added to 55% saturation, and the deposited precipitate was recovered by centrifugation.

The precipitate was dissolved in 2.5 L of the 10 mM tris-acetate buffer (pH 7.5), and passed through a DEAE-cellulose DE52 (Whatman Co.) column (5.2×24 cm) which was previously equilibrated with the same buffer, to allow the enzyme to be adsorbed. After the column was washed with 1.5 L of the same buffer, the enzyme was eluted with a linear increasing concentration of sodium chloride from zero to 0.3 M in the same buffer.

The active fraction was collected, and ammonium sulfate was added to 55% saturation, and then the precipitate was recovered by centrifugation and dissolved in a small amount of the 10 mM tris-acetate buffer (pH 7.5). Then the solution was loaded onto a Sephacryl S-300 (Pharmacia) column (3.4×110 cm), and subjected to gel filtration with the 50 mM tris-acetate buffer (pH 7.5) containing 0.5 M sodium chloride.

The active fraction was concentrated by ultrafiltration using UK-10 membrane (Advantec Toyo) and dialyzed against an approximately 100-fold amount of the 10 mM tris-acetate buffer (pH 7.5). The dialyzed inside solution was passed through a DEAE-Toyopearl (Tosoh Corporation) column (2.2×15 cm) which was previously equilibrated with the same buffer, to allow the enzyme to be adsorbed. Then the column was washed with 150 ml of the same buffer containing 0.1 M sodium chloride, and the enzyme was eluted with a linear increasing concentration of sodium chloride from 0.1 to 0.2 M in the same buffer.

The active fraction was concentrated by ultrafiltration, loaded onto a Sephacryl S-300 column (2.2×101 cm), and subjected to gel filtration.

After sodium chloride was added to the active fraction, to a concentration of 4 M, the solution was passed through a Phenyl-Sepharose (Pharmacia) column (1.6×15 cm) which was equilibrated with the tris-acetate buffer (pH 7.5) containing 4 M sodium chloride, to allow the enzyme to be adsorbed, and then the enzyme was eluted with a linear decreasing concentration of sodium chloride from 4 M to zero in the same buffer. The enzyme obtained was 29 units, and the specific activity thereof was 2.09 unit/mg (calculated in terms of the weight of bovine serum albumin). The purified enzyme did not contain contaminating enzymes such as glycosidase.

The keratan sulfate degrading enzyme obtained above has the following properties.

(1) Action:

The degrading enzyme acts on keratan sulfate and hydrolyzes the N-acetylglucosaminidic linkage thereof.

(2) Substrate specificity:

The degrading enzyme acts on keratan sulfate I, keratan sulfate II, and keratan polysulfate and produces sulfated keratan sulfate disaccharide and sulfated keratan sulfate tetrasaccharide as the main degradation products. Also it is confirmed that the degrading enzyme produces sulfated keratan sulfate pentasaccharide.

(3) Optimum reaction pH:

The degrading enzyme has an optimum reaction pH of from 4.5 to 6 in the 0.1 M acetate buffer or 10 mM tris-acetate buffer at 37° C.

(4) pH Stability:

The degrading enzyme has a pH stability of from 6 to 7 when the degrading enzyme is stood in the 0.1 M acetate buffer or 10 mM tris-acetate buffer at 37° C. for an hour.

(5) Optimum reaction temperature:

The degrading enzyme has an optimum reaction temperature of from 50 to 60° C. when the degrading enzyme reacts in the 0.1 M acetate buffer, pH 6.0, for 10 minutes.

(6) Thermostability:

The degrading enzyme is at least stable at 45° C. or less when the degrading enzyme is stood in the 0.1 M acetate buffer, pH 6.0, for an hour.

The keratan sulfate degrading enzyme obtained in the same manner as described above was used in the following examples. However the present invention is not limited to this enzyme, and other keratan sulfate degrading enzymes of endo-β-N-acetylglucosaminidase type, for example keratanase II, may be used in the present invention.

EXAMPLE 1

50 g of high-sulfated keratan sulfate derived from cartilage of sharks was dissolved in 300 ml of 0.1 M acetate buffer (pH 6.0). To the solution, 25 units of the keratan sulfate degrading enzyme described above was added, and the high-sulfated keratan sulfate was degraded at 37° C. for 24 hours. After the degradation reaction, double the quantity (by volume, and so forth) of ethanol was added to the reaction mixture, and the mixture was stirred and allowed to stand overnight at room temperature. On the following day, the mixture was separated by centrifugation (4,000 rpm, 15 minutes) into the supernatant and precipitate, and the supernatant was concentrated under reduced pressure to give a concentrate (hereinafter referred to as "supernatant A"). On the other hand, the precipitate was dissolved in 300 ml of distilled water, mixed with treble the quantity of ethanol, and stirred. And then the mixture was allowed to stand overnight at room temperature. On the following day, the mixture was separated by centrifugation into the supernatant and precipitate, and the supernatant was concentrated under reduced pressure to give a concentrate (hereinafter referred to as "supernatant B").

The supernatant A was dissolved in a small amount of distilled water, subjected to gel filtration chromatography using Bio-Gel P-2 column (Bio-Rad) (3.6×134 cm) and distilled water as the solvent, and further subjected to ion-exchange chromatography to give the fractions containing the keratan sulfate tetrasaccharide (I), the keratan sulfate pentasaccharide (II), and the keratan sulfate disaccharide (III), respectively. Each of the fractions were freeze-dried.

Each of these keratan sulfate oligosaccharide fractions were dissolved in a small amount of distilled water and further purified by anion-exchange chromatography using Muromac column (Muromachi Kagaku Kogyo) (4.3×35 cm) which was previously equilibrated with distilled water. As the eluent, a saline solution containing a linearly elevated concentration of sodium chloride from zero to 0.3 M was passed through to elute the keratan sulfate tetrasaccharide (I), the keratan sulfate pentasaccharide (II), and the keratan sulfate disaccharide (III), respectively.

Each of the fractions obtained of the keratan sulfate tetrasaccharide (I), the keratan sulfate pentasaccharide (II), and the keratan sulfate disaccharide (III) was concentrated under reduced pressure, desalted by gel filtration chromatography using Cellulofine GCL-25 column (Seikagaku Corporation) (3.2×125 cm), and freeze-dried.

The supernatant B was also treated in the same manner as described above to give the keratan sulfate tetrasaccharide (I), the keratan sulfate pentasaccharide (II), and the keratan sulfate disaccharide (III).

Figure 2:
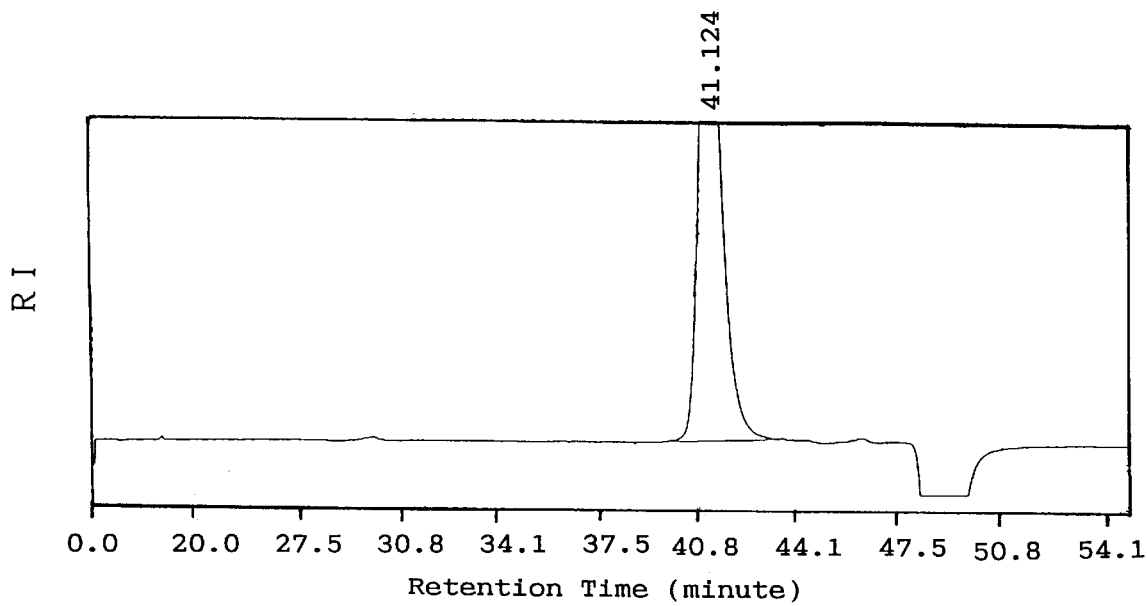
FIG. 2 shows the chromatogram in gel filtration by HPLC of the trisulfated N-acetyllactosamine pentasaccharide (keratan sulfate pentasaccharide (II)) produced in Example 1.
Figure 3:
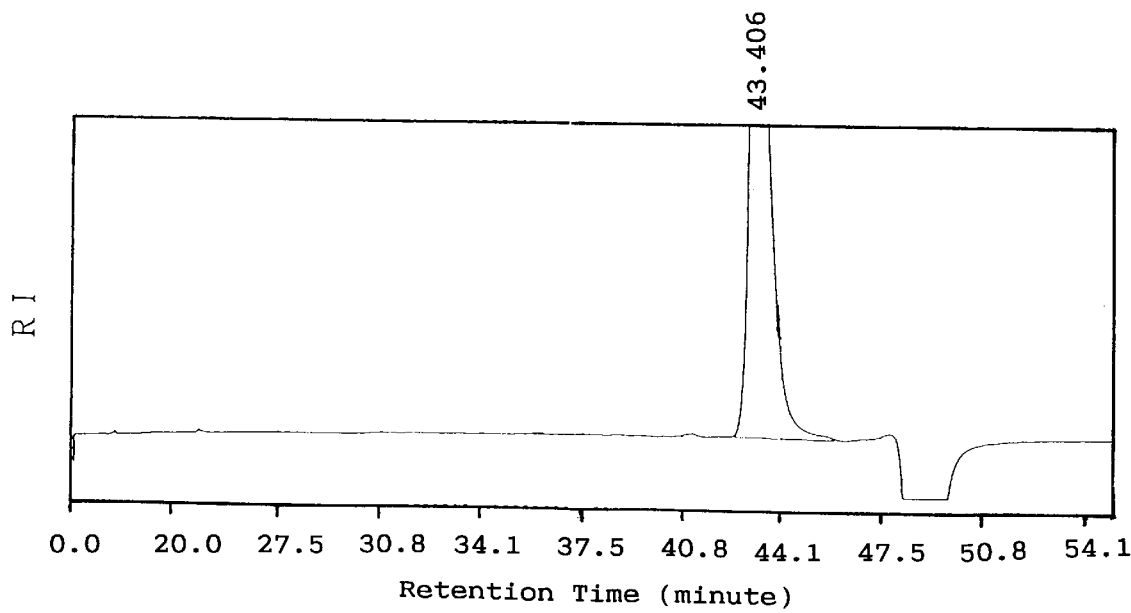
FIG. 3 shows the chromatogram in gel filtration by HPLC of the disulfated N-acetyllactosamine disaccharide (keratan sulfate disaccharide (III)) produced in Example 1.

The chromatogram in gel filtration by HPLC (high performance liquid chromatography) of the keratan sulfate tetrasaccharide (I), the keratan sulfate pentasaccharide (II), and the keratan sulfate disaccharide (III) obtained above are shown in FIG. 1–3, respectively.

From 50 g of the keratan sulfate, 7.8 g (15.6%) of the keratan sulfate tetrasaccharide (I), 1.3 g (2.6%) of the keratan sulfate pentasaccharide(II), and 10.4 g (20.8%) of the keratan sulfate disaccharide (III) were yielded, and none of them contained endotoxin, nucleic acid, protein, protease, and the other glycosaminoglycans.

$^1$H-NMR and $^{13}$C-NMR spectra of the keratan sulfate tetrasaccharide (I), the keratan sulfate pentasaccharide (II), and the keratan sulfate disaccharide (III) obtained above were determined by spectrometers which are JNM-EX400 (400 MHz, JEOL Ltd.) for $^1$H-NMR spectrum and JNM-EX400 (100 MHz, JEOL Ltd.) for $^{13}$C-NMR spectrum, respectively, with sodium 3-(trimethylsilyl)propionate-$D_4$ as an internal standard substance. The chemical shift and coupling constant are represented by δ (ppm) and Hz, respectively. The following shows the results of the determination.

Keratan sulfate tetrasaccharide (I)

$^1$H-NMR δ($D_2O$, 40° C. ): 4.757(1H, d), 4.565(1H, d), 4.561(1H, d), 4.402(1H,d), 4.342(2H, dd), 3.711(1H, dd), 3.626(1H, dd), 3.555(1H, dd), 2.069(3H,s),2.047(3H, s)

$^{13}$C-NMR δ($D_2O$, 25° C.): 177.81, 177.63, 177.30, 105.87, 105.69, 97.84, 93.34, 84.98, 82.41, 81.91, 81.25, 75.55, 75.44, 75.20, 75.13, 75.02, 73.70, 72.68, 72.07, 71.10, 71.01, 70.61, 69.82, 69.59, 69.29, 58.92, 57.94, 56.42, 25.09, 24.76

Keratan sulfate pentasaccharide (II)

Figure 4:
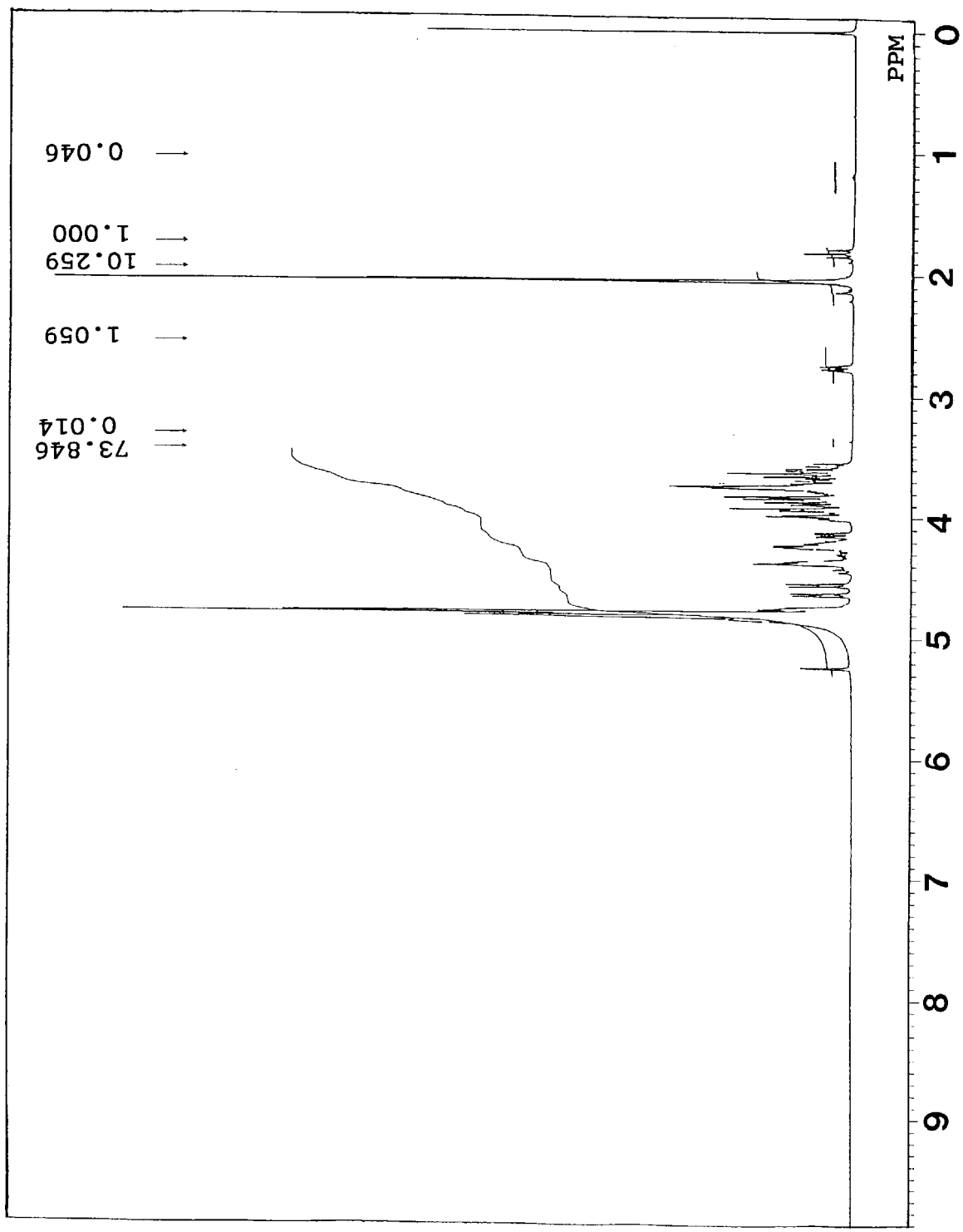
FIG. 4 shows the $^1$H-NMR spectra at 400 MHz of the keratan sulfate pentasaccharide (II) produced in Example 1.

$^1$H-NMR δ($D_2O$, 25° C. ): The chart is shown in FIG. 4.

$^3$C-NMR δ($D_2O$, 25° C.) 177.80, 177.32, 176.86, 105.92, 105.78, 104.94, 102.60, 97.86, 93.32, 85.08, 82.55, 82.04, 79.75, 78.16, 77.93, 75.69, 75.59, 75.48, 75.24, 74.98, 74.36, 72.68, 72.33, 72.07, 71.38, 71.01, 70.65, 70.35, 69.62, 69.13, 65.38, 63.94, 58.92, 57.99, 56.42, 54.57, 42.47, 25.07, 24.93, 24.76

Keratan sulfate disaccharide (III)

$^1$H-NMR δ($D_2O$, 40° C.): 5.235(0.64 H, d, J=1.46 Hz), 4.766(0.41 H, d, J=4.88 Hz), 4.562(1.15 H, d, J=7.82 Hz), 4.44(0.15 H, br), 4.42(0.22 H, br), 4.357(1.30 H, d, J=3.42 Hz), 4.313(0.22 H, d, J=4.88 Hz), 4.286(0.15 H, d, J=3.90 Hz), 4.213(2.37 H, d, J=5.37 Hz), 4.183(0.37 H, t, J=3.42, 2.93 Hz), 4.01–3.97(2.06 H, m), 4.006(d, J=2.44 Hz), 3.927 (1.27 H, d, J=5.37 Hz), 3.86–3.83(0.37 H, br), 3.78–3.69 (2.78 H, m), 3.59–3.56(1.04 H, m), 2.052(3.00 H, m)

$^3$C-NMR δ($D_2O$, 25° C.): 177.61, 177.30, 105.80, 105.63, 97.82, 93.38, 82.02, 81.55, 75.60, 75.47, 75.15, 75.09, 73.70, 72.04, 71.12, 71.07, 69.93, 69.51, 59.00, 56.44, 25.05, 24.76

And the keratan sulfate tetrasaccharide (I), the keratan sulfate pentasaccharide (II), and the keratan sulfate disaccharide (III) obtained above were analyzed by fast atom bombardment mass spectrometry (FABMS).

(1) Cation FABMS (cation fast atom bombardment mass spectrometry)

The keratan sulfate tetrasaccharide (I), the keratan sulfate pentasaccharide (II), and the keratan sulfate disaccharide (III) were dissolved in water to prepare the aqueous solutions at concentrations of 25, 40, and 50 nmol/μl, respectively, and each 1.0 μl of the aqueous solutions was mixed with 1.0 μl of α-thioglycerol (used as a matrix) and used for determination. The determination was run by a triple stage quadrupole mass spectrometer: finnigan MAT TSQ700, with xenon (8 kV) as a bombardment atom. The results are shown in Table 3. The numbers in parentheses in the table represent the relative intensity of peaks (%).

TABLE 3

| Sample | Molecular Relating Ion (m/z) | | | | |
|---|---|---|---|---|---|
| | [M + Na]⁺ | [M + 2Na − H]⁺ | [M + 3Na − 2H]⁺ | [M + 4Na − 3H]⁺ | [M + 5Na − 4H]⁺ |
| Keratan Sulfate Tetrasaccharide (I) | | | | 1157(17) | 1179(100) |
| Keratan Sulfate Pentasaccharide (II) | | | 1324(9) | 1346(14) | 1368(100) 1390(80) |
| Keratan Sulfate Disaccharide (III) | 566(10) | 588(26) | 610(37) | [M − 2H + 3Na − 102]⁺ 508(100) | [M − 2H + 3Na − 102 − 102]⁺ 406(23) |

([M − 2H + 3Na − 102]⁺ and [M − 2H + 3Na − 102 − 102]⁺ are fragment ions.)

(2) Anion FABMS (anion fast atom bombardment mass spectrometry)

The keratan sulfate tetrasaccharide (I), the keratan sulfate pentasaccharide (II), and the keratan sulfate disaccharide (III) were dissolved in water to prepare the aqueous solution at concentrations of 25, 40, and 40 nmol/μl, respectively, and 1.0 μl, 1.0 μl, and 0.5 μl of the aqueous solution of the keratan sulfate oligosaccharide obtained above, respectively, were mixed with 1.0 μl of a-thioglycerol (used as a matrix) and used for determination. The determination was run by a triple stage quadrupole mass spectrometer: finnigan MAT TSQ700, with xenon (8 kV) as a bombardment atom. The results are shown in Table 4. The numbers in parentheses in the table represent the relative intensity of peaks (%).

TABLE 4

| Sample | Molecular Relating Ion (m/z) | | | | |
|---|---|---|---|---|---|
| | [M − H]⁻ | [M + Na − 2H]⁻ | [M + 2Na − 3H]⁻ | [M + 3Na − 4H]⁻ | [M + 4Na − 5H]⁻ |
| Keratan Sulfate Tetrasaccharide (I) | | | 1111(11) | 1133(100) | |
| Keratan Sulfate Pentasaccharide (II) | | | | 1322(22) | 1344(100) 1366(7) |
| Keratan Sulfate Disaccharide (III) | 542(5) | 564(100) | 586(6) | [M + Na − 2H − 102]⁻ 462(23) | |

([M + Na − 2H − 102]⁻ is a fragament ion.)

Moreover, the contents of endotoxin, nucleic acid, protein, and protease in the purified keratan sulfate tetrasaccharide (I), keratan sulfate pentasaccharide (II), and keratan sulfate disaccharide (III) which were obtained above were determined. The results are shown in Table 5.

TABLE 5

| | Keratan Sulfate Tetrasaccharide (I) | Keratan Sulfate Pentasaccharide (II) | Keratan Sulfate Disaccharide (III) |
|---|---|---|---|
| Endotoxin[a] | 6.5 pg/mg or less 1.9 × 10⁻² EU/mg or less | 0.2 pg/mg or less 5.8 × 10⁻⁴ EU/mg or less | 0.2 pg/mg or less 5.8 × 10⁻⁴ EU/mg or less |
| Nucleic Acid[b] | 21.0 pg/mg or less | 21.0 pg/mg or less | 21.0 pg/mg or less |
| Protein[c] | 1.8 μg/mg or less | 1.8 μg/mg or less | 1.8 μg/mg or less |
| Protease[d] | less than detection limit | less than detection limit | less than detection limit |

Note)
[a]: The content of endotoxin per mg of keratan sulfate oligosaccharide was determined by Toxicolor (trade name) system (Seikagaku Corporation). EU represents Endotoxin Unit.
[b]: The content of nucleic acid was determined concerning DNA by the threshold method (DNA analyzer: Threshold (Molecular Device, US)).
[c]: The content of protein was determined by the Lowry method with bovine serum albumin as a standard.
[d]: The content of protease was determined with FITC-casein as a substrate.

The contents of glycosaminoglycans such as hyaluronic acid, chondroitin sulfate, dermatan sulfate, heparan sulfate, keratan sulfate, and the like in the purified keratan sulfate tetrasaccharide (I), keratan sulfate pentasaccharide (II), and keratan sulfate disaccharide (III) were determined by electrophoresis with a cellulose acetate membrane (Cepallax, Fuji Photo Film) (buffer: 0.1 M pyridine.formic acid; pH 3.0; current: 0.5 mA/cm; electrophoresis period: 30 minutes; staining: 0.5% Alucian Blue solution). As the result none of the compounds were detected in each keratan sulfate oligosaccharide (less than detection limit).

EXAMPLE 2

The keratan sulfate tetrasaccharide (I), the keratan sulfate pentasaccharide (II), and the keratan sulfate disaccharide (III) obtained above were subjected to the acute toxicity test and a variety of pharmacological tests.

<Acute toxicity test>

The purified keratan sulfate oligosaccharides which were prepared in Example 1, respectively, were subjected to the acute toxicity test with male and female ICR mice of five weeks old. The PBS (phosphate-buffered saline) solution of the keratan sulfate tetrasaccharide (I), the keratan sulfate pentasaccharide (II), and the keratan sulfate disaccharide (III), respectively, were intravenously administered in 1,000 mg/kg or 2,000 mg/kg dose, and then observation of general appearance and mortality, and body weight measurement were carried out for 14 days. After that, the animals were sacrificed and autopsied.

As a result, none of the animals died and no abnormality in the general appearance, body weight, and autopsy was observed.

From the results obtained above, it was concluded that the minimum lethal dose of the keratan sulfate oligosaccharide described above even by intravenous administration is more than 2,000 mg/kg.

<Anti-inflammation test>

(1) Anti-inflammation test with rabbit of papain-induced arthritis model

The anti-inflammatory effect of the keratan sulfate oligosaccharide with rabbits of the papain-induced arthritis model was examined using the volume of synovial fluid as an indication.

(1-1) Anti-inflammatory effect on bilateral arthritis model of keratan sulfate tetrasaccharide by intra-articular administration Into the articular cavity of both knee joint of Japanese white rabbits (female) of 3 kg weight, 150 $\mu$l of the saline solution of papain (1%) was injected to prepare the arthritis model. One day after injecting papain, 150 $\mu$l of the PBS solution of the purified keratan sulfate tetrasaccharide (I) (1% solution; 1.5 mg/joint) which was prepared in Example 1 was injected into the articular cavity of the left joint (hereinafter referred to as "the keratan sulfate tetrasaccharide (I) administered foot"), and 150 $\mu$l of PBS was injected into that of the right joint (hereinafter referred to as "the keratan sulfate tetrasaccharide (I) unadministered foot"). Hereinafter the rabbits subjected to administration of the keratan sulfate tetrasaccharide (I) are referred to as "the administered group". And the rabbits subjected to the papain injection only (hereinafter referred to as the control group) and the normal rabbits not subjected to the papain injection (hereinafter referred to as the normal group) were also examined in the same manner hereinafter.

Seven days after the injection, the blood was drawn from the auricular artery, and plasma containing heparin was separated. After drawing the blood, the rabbits were anatomized and the both knee joint were separated. The articular cavity was washed with 2 ml of saline three times to recover the synovial fluid. The calcium concentrations in the plasma and the recovered synovial fluid were determined, and the volume of synovial fluid was calculated from the following formula.

Volume of Synovial Fluid (ul/articulation)=Amount of Calcium in Recovered Synovial Fluid ($\mu$g/articulation)/Concentration of Calcium in Plasma ($\mu$g/$\mu$l)

The results obtained above are shown in Table 6. In the table, "n" represents the number of rabbits in each group used in the experiment.

TABLE 6

| | Control Group (n = 12) | Administered Group (n = 8) | | Normal Group (n = 8) |
| --- | --- | --- | --- | --- |
| | | Administered Foot | Unadministered Foot | |
| Volume of Synovial Fluid ($\mu$l) | 729 | 530 | 537 | 437 |
| (Standard Deviation) | (111) | (147) | (130) | (63.3) |
| Significance* | — | $p < 0.05$ | $p < 0.05$ | $p < 0.01$ |

Note)
*: Significance is given by the Duncan multiple comparative test.

As apparent from these results, the volume of synovial fluid in the administered group of the keratan sulfate tetrasaccharide (I) of the present invention was significantly less than that in the control group, and therefore the improvement function on arthritis of the keratan sulfate tetrasaccharide (I) has been confirmed.

(1-2) Anti-inflammatory effect on bilateral arthritis model of keratan sulfate tetrasaccharide by intramuscular administration The arthritis model was prepared by the method described in (1-1), and one day after injecting papain, 150 $\mu$l of the PBS solution of the purified keratan sulfate tetrasaccharide (I) (1% solution; 0.5 mg/kg weight) which was prepared in Example 1 was injected into the hip muscle of the left side (hereinafter referred to as "the keratan sulfate tetrasaccharide (I) administered group"). As the control, 150 $\mu$l of PBS was injected to the arthritis model instead of the PBS solution of the keratan sulfate tetrasaccharide (I) and hereinafter these rabbits are referred to as "the control group". And the normal rabbits not subjected to the papain injection (hereinafter referred to as "the normal group") were also examined in the same manner hereinafter. Seven days after the injection, the volume of synovial fluid was calculated in the same manner as in (1-1).

The results obtained above are shown in Table 7. In the table, "n" represents the number of rabbits in each group used in the experiment.

TABLE 7

| | Control Group (n = 12) | Administered Group (n = 12) | Normal Group (n = 8) |
| --- | --- | --- | --- |
| Volume of Synovial Fluid ($\mu$l) | 729 | 561 | 437 |
| (Standard Deviation) | (111) | (65.8) | (63.3) |
| Significance* | — | $p < 0.01$ | $p < 0.01$ |

Note)
*: Significance is given by the Duncan multiple comparative test.

As apparent from these results, the volume of synovial fluid in the administered group of the keratan sulfate tetrasaccharide (I) of the present invention was significantly less than that in the control group, and therefore the improvement function on arthritis of the keratan sulfate tetrasaccharide (I) has been confirmed. (1-3) Anti-inflammatory effect on unilateral arthritis model of keratan sulfate tetrasaccharide by intramuscular administration Into the articular cavity of left joint of Japanese white rabbits (female) of 3 kg weight, 150 $\mu$l of the saline solution of papain (1%) was injected, and the right joint was not treated to prepare the unilateral arthritis model. One day after injecting papain, 150 $\mu$l of the PBS solution of the purified keratan sulfate tetrasaccharide (I) (2%, 1%, and 0.5% solution; 1.0 mg/kg, 0.5 mg/kg, and 0.25 mg/kg, respectively) which was prepared in Example 1 was injected into the hip muscle of the left side (hereinafter referred to as "the keratan sulfate tetrasaccharide (I) administered group"). As the control, 150 μl of PBS was injected to the arthritis model instead of the PBS solution of the keratan sulfate tetrasaccharide (I) and hereinafter these rabbits are referred to as "the control group". And the normal rabbits not subjected to the papain injection (hereinafter referred to as "the normal group") were also examined in the same manner hereinafter. Seven days after the injection, the volume of synovial fluid was calculated in the same manner as in (1-1).

The results obtained above are shown in Table 8. In the table, "n" represents the number of rabbits in each group used in the experiment.

TABLE 8

| | Control Group | Keratan Sulfate Tetrasaccharide (I) Administered Group (mg/kg) | | | Normal |
|---|---|---|---|---|---|
| | PBS (n = 10) | 0.25 (n = 9) | 0.5 (n = 10) | 1.0 (n = 9) | Group (n = 10) |
| Volume of Synovial Fluid (μl) | 722 | 619 | 597 | 528 | 433 |
| (Standard Deviation) | (70.0) | (70.6) | (68.9) | (53.1) | (46.1) |
| Significance* | — | p < 0.05 | p < 0.01 | p < 0.01 | p < 0.01 |

Note)
*: Significance is given by the TUKEY multiple comparative test.

As apparent from these results, the volume of synovial fluid in the administered group of the keratan sulfate tetrasaccharide (I) of the present invention was significantly less than that in the control group, and therefore the improvement function on arthritis of the keratan sulfate tetrasaccharide (I) has been confirmed.

Figure 5:
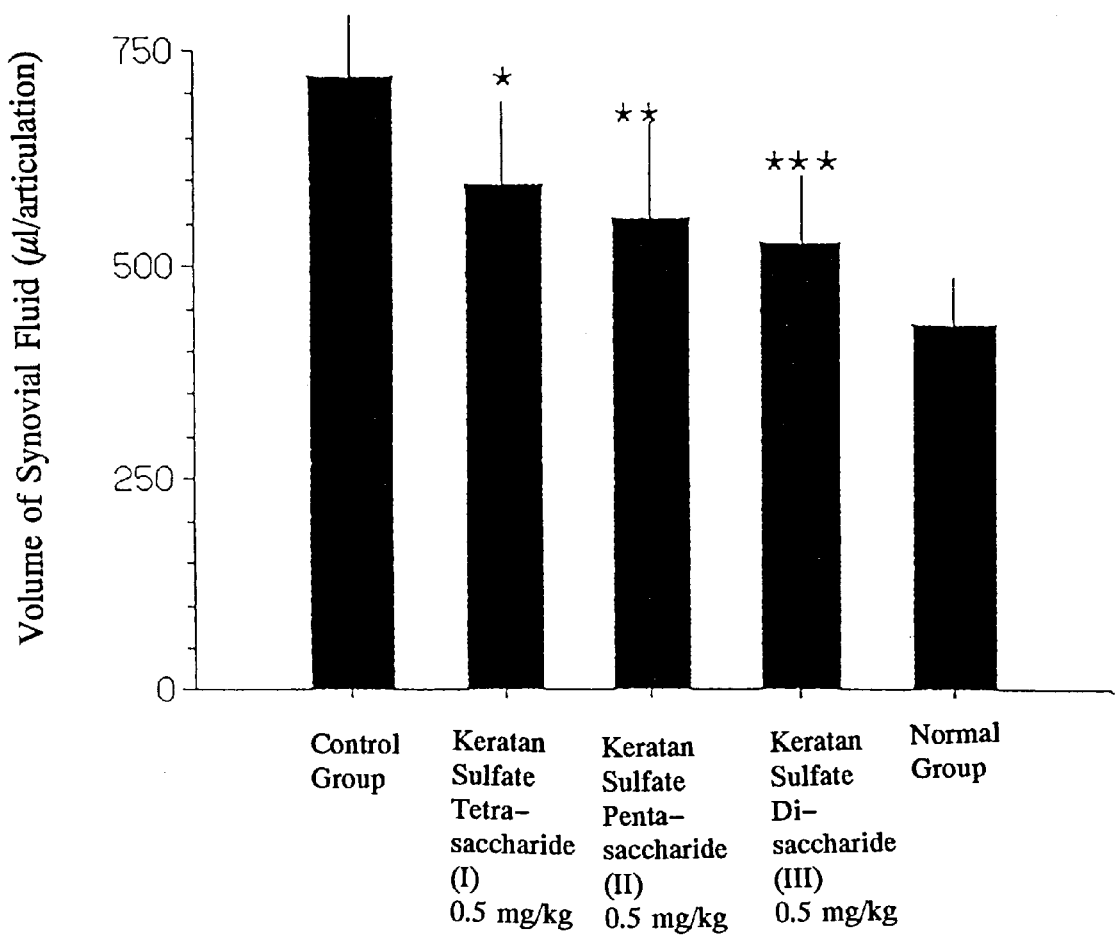
FIG. 5 is a graph showing the volume of synovial fluid of the papain arthritis model rabbits subjected to administration of the keratan sulfate tetrasaccharide (I), the keratan sulfate pentasaccharide (II), or the keratan sulfate disaccharide (III).

(1-4) Anti-inflammatory effect on unilateral arthritis model of varieties of keratan sulfate oligosaccharide by intramuscular administration The examination was performed in the same manner as in (1-3) except for using 150 μl of the PBS solution of the purified keratan sulfate tetrasaccharide (I), the keratan sulfate pentasaccharide (II), and the keratan sulfate disaccharide (III) (1% solution; 0.5 mg/kg) which were prepared in Example 1. The results are shown in FIG. 5. In the figure, *, , and * represent that they have the significant difference with p<0.05, p<0.01, and p<0.001, respectively. And in each group, 10 rabbits were used for the examination.

From these results, the quantity of synovial fluid in any of the administered groups of the keratan sulfate tetrasaccharide (I), the keratan sulfate pentasaccharide (II), and the keratan sulfate disaccharide (III) was significantly less than that in the control group, and therefore the improvement function on arthritis of each of the keratan sulfate oligosaccharide described above has been confirmed.

(2) Anti-inflammation test with foot edema reversed passive Arthus reaction of rat The effect of the keratan sulfate oligosaccharide was examined on the foot edema reversed passive Arthus reaction of rats, which is a type III allergic inflammation model. That is, the rabbit antiovalbumin serum was subcutaneously administered to the planta of the rats which were previously subjected to the administration of the test substances, furthermore ovalbumin was administered by injection into the caudal vein thereof to induce inflammation (edema), and the inhibitory effect on edema of the test substances was examined.

(Administration of test substances)

Male Crj:SD rats of five weeks old were subjected to a fast of about 17 hours after a week period of quarantine, and, before inducing inflammation, subjected to the administration of the purified keratan sulfate tetrasaccharide (I) which was prepared in Example 1, indomethacin (Sigma; Lot No. 19F0018), or dexamethasone (Banyu Pharmaceutical); Decadron injection; Lot No. 8D307P) as the test substances, or saline (Otsuka Pharmaceutical; Lot No. K3H72) as the negative control. The keratan sulfate tetrasaccharide (I) and dexamethasone were dissolved in saline, respectively, and the indomethacin was dissolved in 0.5% sodium carboxymethylcellulose (CMC-Na; Wako Pure Chemical Industries; Lot No. PTN1418) in use. The volume of dose was 0.5 ml per 100 g weight in each test. Concerning the route of administration, the keratan sulfate tetrasaccharide (I), saline, and dexamethasone were administered from the caudal vein, and the indomethacin was orally administered. And the substances except for indomethacin were administered by the blind method.

The dose and administration schedule of each test substance were as follows. Each group consisted of five animals.

(i) Administration at five minutes before inducing inflammation
  (1) Saline (negative control)
  (2) Keratan sulfate tetrasaccharide (I) 1 mg/kg
  (3) Keratan sulfate tetrasaccharide (I) 3 mg/kg
  (4) Keratan sulfate tetrasaccharide (I) 10 mg/kg
(ii) Administration at 30 minutes before inducing inflammation
  (5) Indomethacin (positive control) 5 mg/kg
(iii) Administration at three hours before inducing inflammation
  (6) Keratan sulfate tetrasaccharide (I) 1 mg/kg
  (7) Keratan sulfate tetrasaccharide (I) 3 mg/kg
  (8) Keratan sulfate tetrasaccharide (I) 10 mg/kg
  (9) Dexamethasone (positive control) 1 mg/kg (Induction of inflammation)

The rabbit antiovalbumin serum was subcutaneously administered to each of the rats described above on the planta thereof, and ovalbumin was further administered by injection into the caudal vein to induce inflammation foot edema. The antiserum used was prepared as follows. That is, to the regions of back of rabbits, 1 ml of the equivalently mixed solution (emulsion) of the saline containing 2% ovalbumin (10 mg per one animal, Egg Albumin 5×Cryst, Lot No. P93601; Seikagaku Corporation) and the Freund's complete adjuvant (FCA) was intradermally injected once a week three times totally to subject themselves to sensitization. About 34 days after the last sensitization, the blood was drawn to obtain the antiserum. The antibody titer of the antiserum obtained was determined by the double layer method. Namely, the determination was performed using the white precipitation reaction of the antiserum diluted with saline and the saline containing 0.1% ovalbumin (1 mg/ml) as the indicator. As a result, the antibody titer of the antiserum obtained was x$2^7$.

Figure 6:
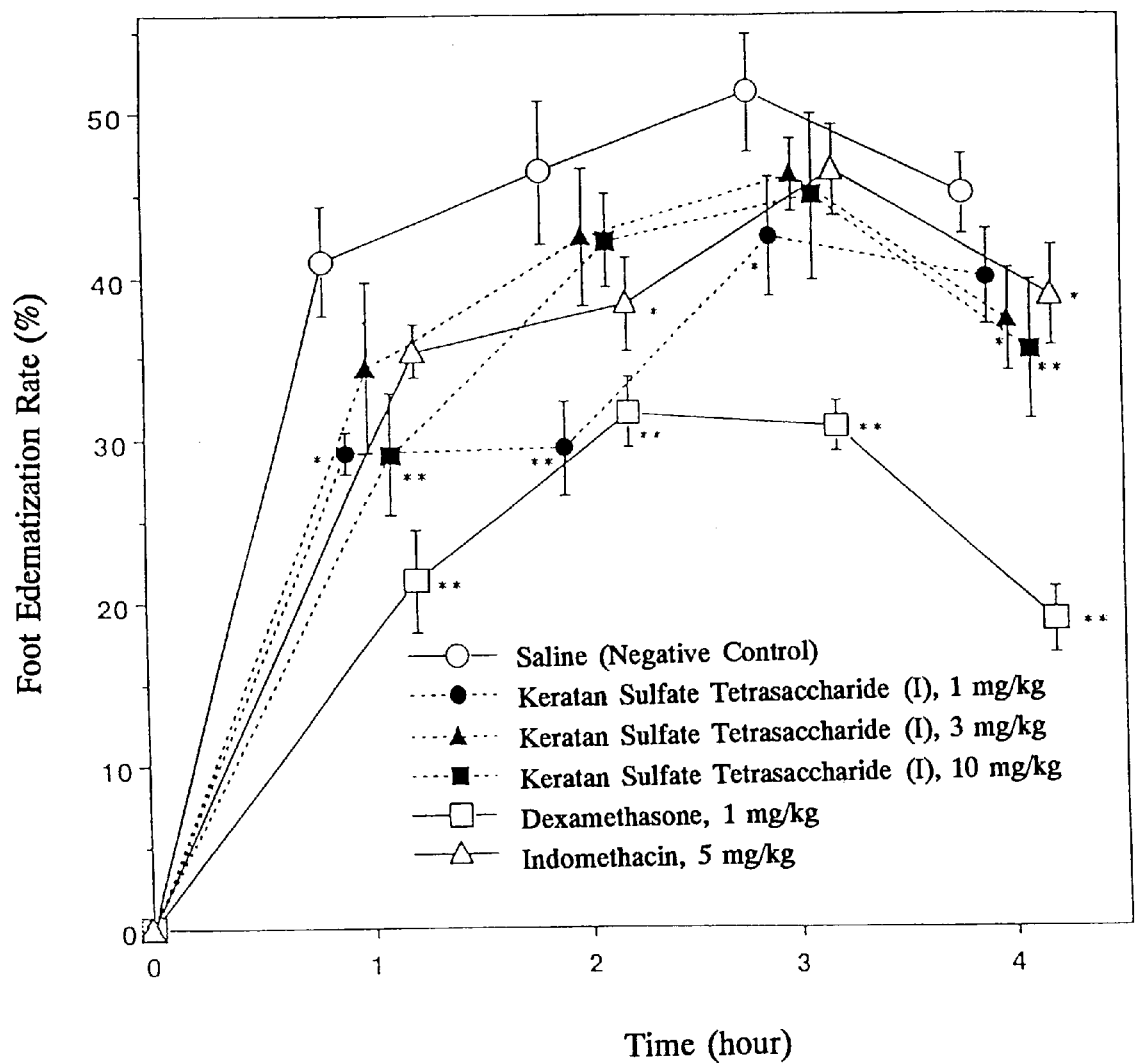
FIG. 6 is a graph showing the change on standing of the edematization rate in feet of rats subjected to induction of inflammation when the keratan sulfate tetrasaccharide (I) or varieties of the test substances is administered to the rats at five minutes before inducing inflammation.
Figure 7:
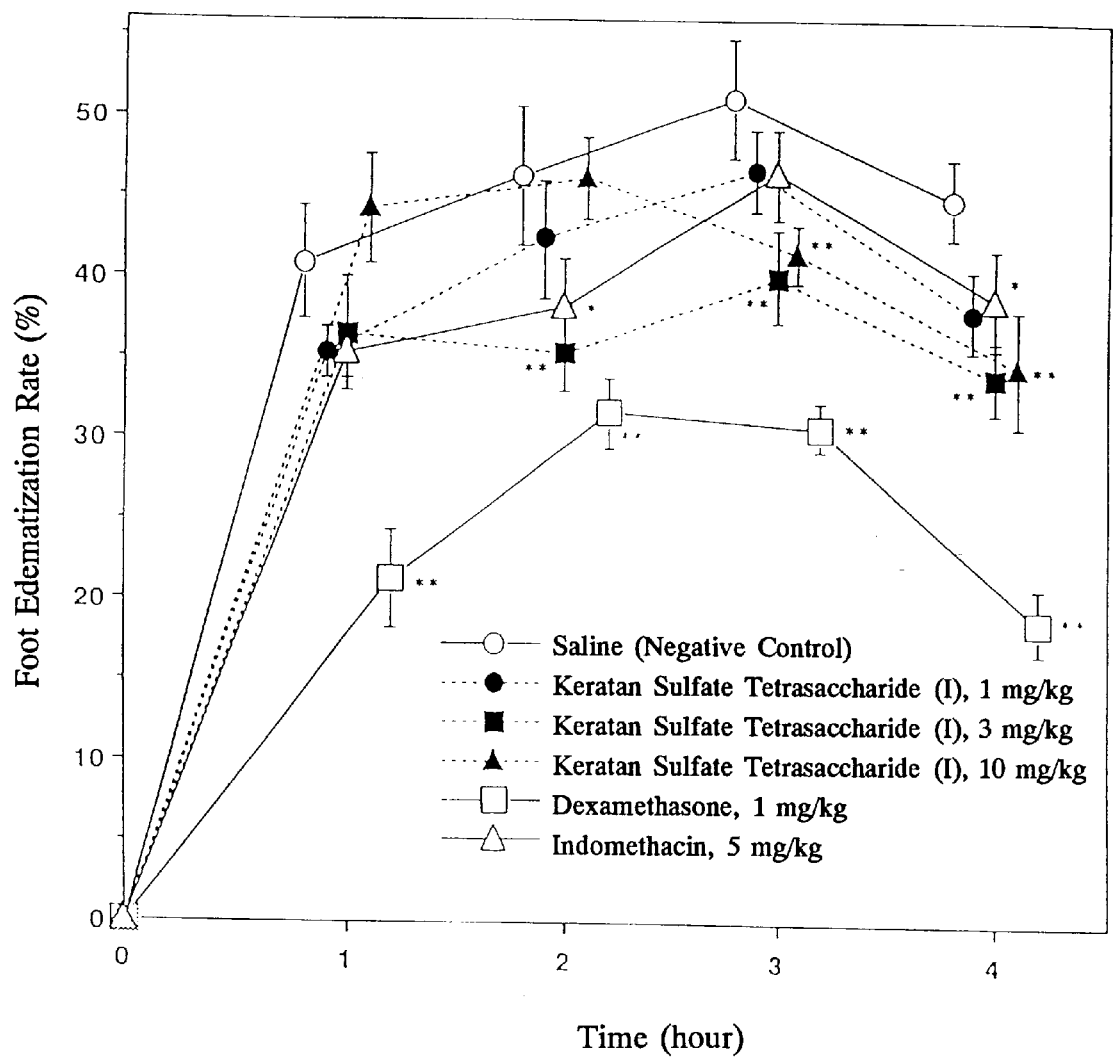
FIG. 7 is a graph showing the change on standing of the edematization rate in feet of the rats subjected to induction of inflammation when the keratan sulfate tetrasaccharide (I) or varieties of the test substances is administered to the rats at three hours before inducing inflammation.

After the period which is designed for each group, each 0.1 ml of the sixfold diluted antiserum was subcutaneously administered to the planta of left rear foot of the rats which were subjected to the administration of each test substance. Then, the saline containing 0.5% ovalbumin (25 mg/5 ml/kg) was administered into the caudal vein to induce inflammation. The volume of the treated feet in each group was determined before inducing inflammation, and one, two, three and four hours after inducing inflammation by a foot volume determining device (TK-101, Unicom) to yield the foot edematization rate from the difference from the value before the induction, and the edematization inhibitory rate of the test substance administered group to the control group was calculated. In each edematization rate obtained, the difference between the averages was tested by the minimum significant difference test. The foot edematization rate and the edematization inhibitory rate of each administered group are shown in Table 9, and the foot edematization rate of the administered groups which was subjected to the administration of the agent at five minutes and at three hours before inducing inflammation are shown in FIG. 6 and FIG. 7, respectively. In the figures, *, and ** represent that they have the significant difference with p<0.05, and p<0.001, respectively.

after four hours. And in the dexamethasone administered group, significantly low values were observed at any determination point between one and four hours after inducing inflammation.

The foot edematization inhibitory rate in the indomethacin administered group was from 9% to 17.5% after from one to four hours, while that in the keratan sulfate tetrasaccharide (I) administered groups of the administration before five minutes was calculated to be as high as from 8.6% to 36.5%. And in the keratan sulfate tetrasaccharide (I) administered groups of the administration before three hours, the inhibitory rate was from −8.1% to 24.4%. On the other hand, in the dexamethasone administered group, the foot edematization inhibitory rate was as high as from 31.7% to 58.1%.

(3) Anti-inflammation test with carrageenin pleurisy model of rat

TABLE 9

| Test Substance | Dose (mg/kg) | 1 Hour Later Edematization Rate (%) Inhibitory Rate (%) | | 2 Hours Later Edematization Rate (%) Inhibitory Rate (%) | | 3 Hours Later Edematization Rate (%) Inhibitory Rate (%) | | 4 Hours Later Edematization Rate (%) Inhibitory Rate (%) | |
|---|---|---|---|---|---|---|---|---|---|
| Saline (Control) | — | 40.9 ± 3.4 | | 46.3 ± 4.4 | | 51.2 ± 3.7 | | 44.9 ± 2.5 | |
| Keratan Sulfate Tetrasaccharide (I) | 1 | 29.2 ± 1.3** | (28.7) | 29.4 ± 2.9** | (36.5) | 42.3 ± 3.6** | (17.0) | 39.8 ± 3.0 | (11.3) |
| Administration at 5 Minutes Before | 3 | 34.4 ± 5.2 | (15.8) | 42.3 ± 4.2 | (8.6) | 46.1 ± 2.2 | (9.5) | 37.2 ± 3.1* | (17.1) |
| Inducing Edema | 10 | 29.1 ± 3.7** | (28.9) | 42.1 ± 2.9 | (9.1) | 44.8 ± 5.1 | (12.3) | 35.4 ± 4.3** | (21.2) |
| Indomethacin Oral Administration at 30 Minutes Before Inducing Edema | 5 | 35.4 ± 1.6 | (13.5) | 38.2 ± 2.9* | (17.5) | 46.4 ± 2.8 | (9.0) | 38.7 ± 3.1* | (13.8) |
| Keratan Sulfate Tetrasaccharide (I) | 1 | 35.4 ± 1.6 | (13.4) | 42.4 ± 3.6 | (8.4) | 46.7 ± 2.6 | (8.4) | 38.0 ± 3.5* | (15.5) |
| Administration at 3 Hours Before | 3 | 36.5 ± 3.5 | (10.6) | 35.3 ± 2.3** | (23.9) | 40.1 ± 2.8** | (21.5) | 33.9 ± 2.2** | (24.4) |
| Inducing Edema | 10 | 44.2 ± 3.4 | (−8.1) | 46.1 ± 2.6 | (0.4) | 41.5 ± 1.8** | (18.7) | 34.5 ± 3.6** | (23.2) |
| Dexamethason Administration at 3 hours Before Inducing Edema | 1 | 21.3 ± 3.1** | (47.8) | 31.6 ± 2.2** | (31.7) | 30.7 ± 1.5** | (39.9) | 18.8 ± 2.0** | (58.1) |

* and ** represents that they have significant difference with P < 0.05 (*) and P < 0.01 (**) respectively to control.

As a result, the foot edematization rate after an hour in the saline administered group which was the negative control was 40.9%, while that in the keratan sulfate tetrasaccharide (I) administered groups of the administration at five minutes before inducing inflammation was from 29.1% to 34.4%, and the significant difference was observed in the 1 mg/kg administered group and the 10 mg/kg administered group. Although dose-dependent reaction was not observed on and after an hour after inducing inflammation, the foot edematization rate in the 3 mg/kg administered group and the 10 mg/kg administered group was 37.2% and 35.4%, respectively, which were significantly low even after four hours. And in the keratan sulfate tetrasaccharide (I) administered groups of the administration at three hours before inducing inflammation, although significant difference was not observed an hour after inducing inflammation, significantly low values were observed in the 3 mg/kg administered group after two hours, the 10 mg/kg administered group after three hours, and the 1 mg/kg administered group after four hours of which the values were 35.3%, 41.5%, and 38%, respectively. In the indomethacin administered group, significantly low values were observed after two hours and The effect of the keratan sulfate oligosaccharide was examined with the carrageenin pleurisy model of rats which is generally used for evaluation of anti-inflammatory agents.

Female S.D. rats (n=37) of about 150 to 170 g weight were used for the test. The λ-carrageenin (Sigma) was dissolved in saline to a concentration of 2%, and the solution was filtered with a 0.8 μm filter. The carrageenin solution obtained was intrathoracically administered at 100 μl/animal to prepare the pleurisy model.

To the pleurisy model of rats (n=19) described above, the keratan sulfate tetrasaccharide (I) dissolved in PBS was subcutaneously (s.c.) administered in 20 mg/kg or 10 mg/kg dose. And as the positive control, steroid (dexamethasone acetate; Banyu Pharmaceutical) was subcutaneously administered to the eight rats described above in 150 μg/kg which was the clinical dose. As the negative control, PBS was subcutaneously administered to the 10 rats. Each administration was carried out immediately after the administration of carrageenin. The administrated groups are summarized in Table 10.

TABLE 10

| Administrated Group | Test Substance | Dose | Administration Route |
|---|---|---|---|
| (1) n = 10 | Keratan Sulfate Tetrasaccharide (I) | 2 mg/ml 10 mg/kg | s.c. |
| (2) n = 9 | Keratan Sulfate Tetrasaccharide (I) | 4 mg/ml 20 mg/kg | s.c. |
| (3) n = 8 | Dexamethasone Acetate | 30 μg/ml 150 μg/kg | s.c. |
| (4) n = 10 | PBS (Negative Control) | | s.c. |

Each rat was anatomized six hours after the administration of λ-carrageenin. The thoracic cavity of the rats was opened to collect the retained pleural fluid using a 2-ml syringe with probe. After that, inside of the thoracic cavity was washed with 1 ml of saline, and the washing solution was recovered. The volume of the pleural fluid recovered with the syringe was determined, and the number of leukocyte (cell number) in the pleural fluid was determined by an automatic cytometer. The results are be shown in FIG. 8 and FIG. 9, respectively. In the figures, * and ** represent that they have the significant difference with p<0.05 and p<0.01, respectively (wherein "p" means a level of significance by the Duncan test).

Figure 8:
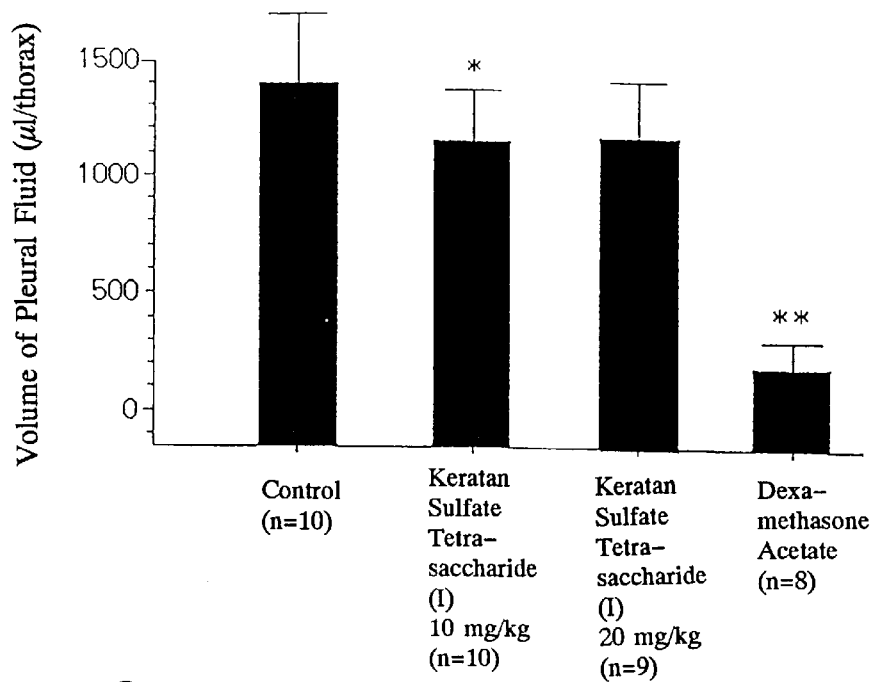
FIG. 8 is a graph showing the volume of pleural fluid of the carrageenin pleurisy model rats subjected to administration of the keratan sulfate tetrasaccharide (I) or dexamethasone acetate.
Figure 9:
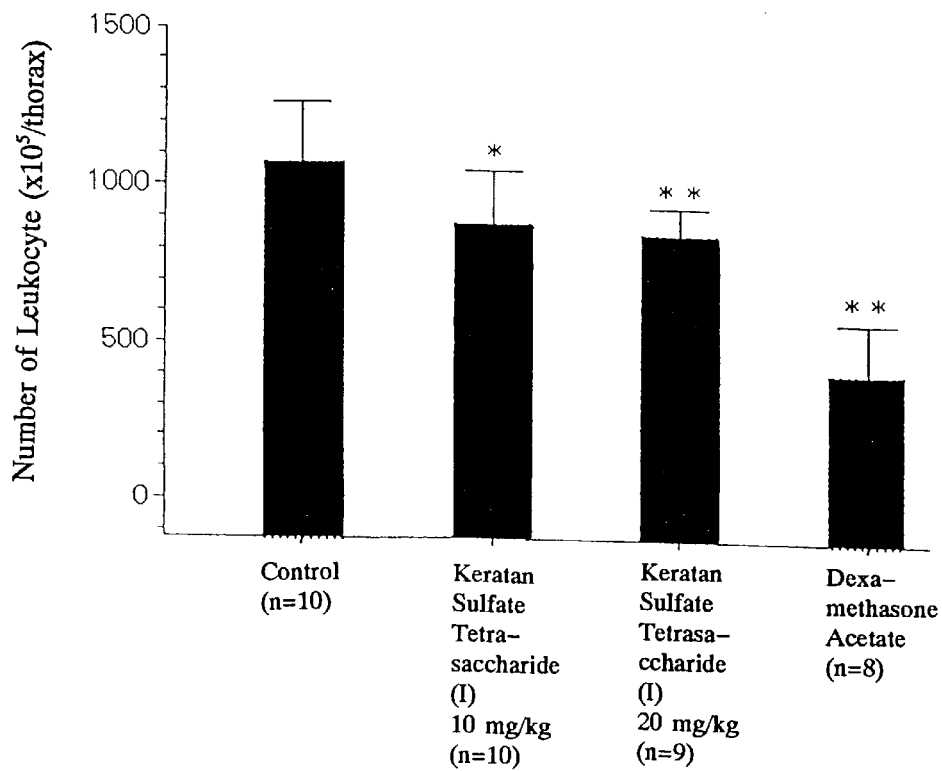
FIG. 9 is a graph showing the number of leukocyte in pleural fluid of the carrageenin pleurisy model rats subjected to administration of the keratan sulfate tetrasaccharide (I) or dexamethasone acetate.

As shown in FIG. 8, the volume of pleural fluid in the keratan sulfate tetrasaccharide (I) 10 mg/kg administered group was significantly less than that in the negative control group, but almost same as that in the keratan sulfate tetrasaccharide (I) 20 mg/kg administered group, and therefore, dose dependence was not observed. The quantity of the pleural fluid in the dexamethasone acetate administered group was significantly less than that in the negative control group. And the number of leukocyte in the pleural fluid in each of the keratan sulfate tetrasaccharide (I) 10 mg/kg and 20 mg/kg administered groups was significantly less than that in the negative control group, and dose-dependent decrease was observed in the number of leukocyte (See FIG. 9.). The number of leukocyte in the dexamethasone acetate administered group was significantly less than that in the control group. (See FIG. 9.) From the results described above, the anti-inflammatory effect on the carrageenin pleurisy model of rats of the keratan sulfate tetrasaccharide (I) has been confirmed.

(4) Inhibitory effect for generation of active oxygen ($O_2^-$) in neutrophile of guinea pig To female Hartley guinea pigs of five weeks old (purchased from Japan SLC), 20 ml of the 0.2% aqueous solution of glycogen (Type II; Oyster; Sigma) dissolved in saline which was previously sterilized with autoclave, was intraperitoneally administered. The guinea pigs were sacrificed by bleeding 16 hours after the administration, and 20 ml of the saline containing heparin at a concentration of 10 U/ml was intraperitoneally injected to recover the peritoneal exudate. Hereinafter all the operations were carried out under ice-water cooling condition except for incubation. The recovered exudate was centrifuged at 1,000 rpm for 10 minutes, the precipitate obtained was hemolyzed with purified water for 30 seconds, and returned into isotonicity with the Hanks' solution at double the concentration (not containing phenol red; Nissui Seiyaku), and further it was centrifuged at 1,000 rpm for 10 minutes. The precipitate obtained was suspended in the Hanks' solution and centrifuged and the operations were repeated once more to give the neutrophile.

The collected neutrophile of the guinea pigs was suspended in the Hanks' solution, the number of leukocyte in the suspension was determined by a cytometer (System K-2000; Toa Iyo Denshi Co.), and the suspension diluted with the Hanks' solution to $2 \times 10^6$ cells/ml was used in the determination as the cell suspension. After mixing 1 ml of the cell suspension and 10 μl of the purified keratan sulfate oligosaccharide (keratan sulfate tetrasaccharide (I), the keratan sulfate pentasaccharide (II), or the keratan sulfate disaccharide (III)) prepared in Example 1 described above, and the mixture was preincubated at 37° C. for an hour. After that, to it 50 μl of the 1.6 mM cytochrome c (Type III; Horse Heart; Sigma), and 10 μl of the 100 μM N-formyl-Met-Leu-Phe (hereinafter sometimes referred to as "FMLP"; Sigma) were added in order and mixed. After the mixture was incubated at 37° C. for 10 minutes, cooled with ice to stop the reaction, and centrifuged at 3,000 rpm for five minutes.

Figure 10:
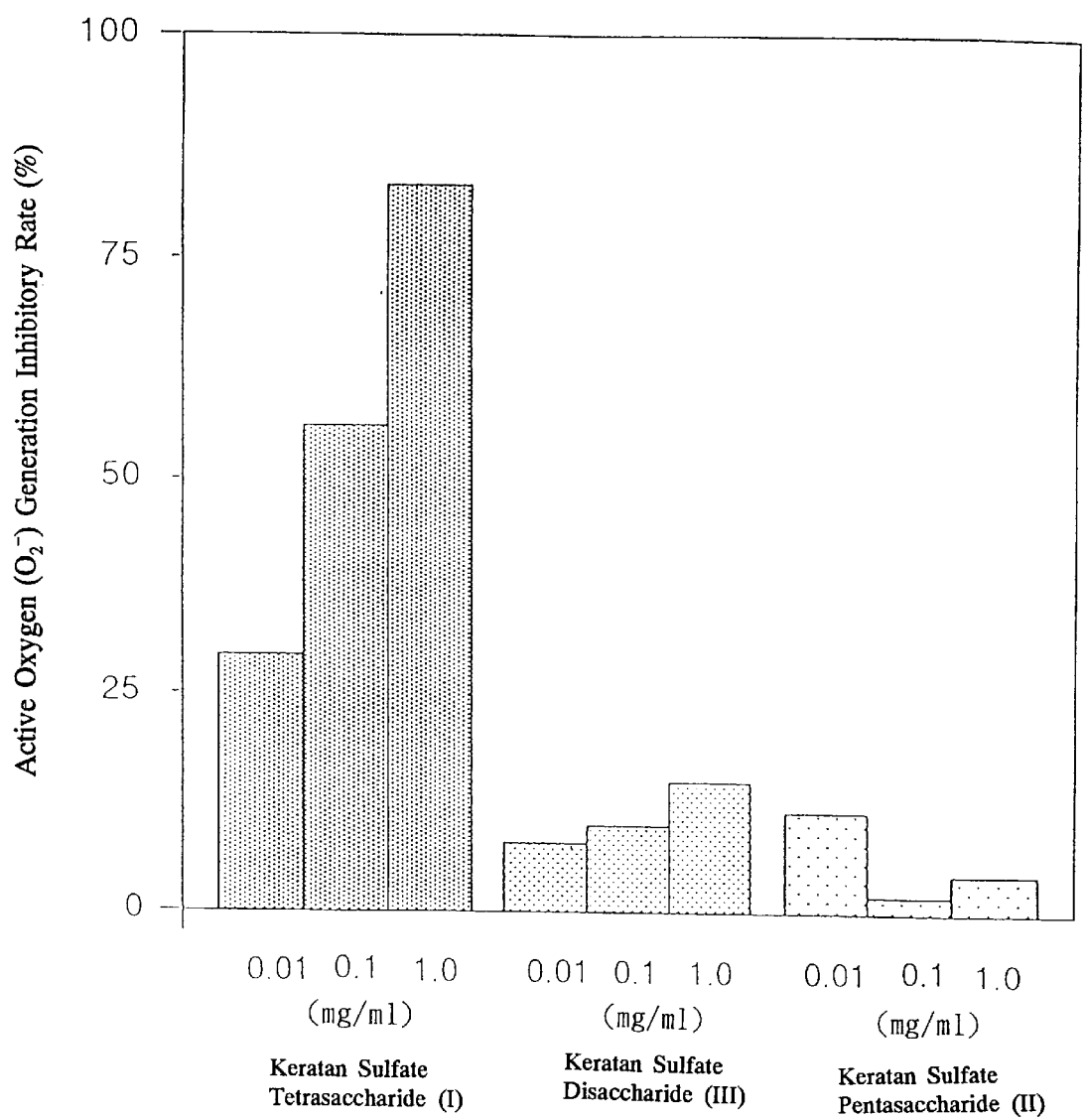
FIG. 10 is a graph showing the inhibitory effect for active oxygen ($O_2-$) generation of the keratan sulfate tetrasaccharide (I), the keratan sulfate pentasaccharide (II), and the keratan sulfate disaccharide (III) to the neutrophile of guinea pigs which is stimulated with N-formyl-Met-Leu-Phe (FMLP).

The supernatant obtained by the centrifugation was separated and the absorbance thereof was determined at 550 nm to estimate the quantity of reducing cytochrome c per $2 \times 10^6$ cells after the 10 minutes incubation. The quantity of reducing cytochrome c increases with the generation of active oxygen ($O_2^-$). In the determination, the sample with addition of recombinant human SOD (superoxide dismutase) to a final concentration of 20 μg/ml was used as a blank. In the experiment, six guinea pigs were independently used. The proportion of the quantity of reducing cytochrome c of each keratan sulfate oligosaccharide added group was calculated by defining the quantity of reducing cytochrome c of the control (without addition of the keratan sulfate oligosaccharide) as 100%, and the difference from the quantity of the control group was calculated as the inhibitory rate (%) for generation of active oxygen ($O_2^-$), and moreover, the averages in each experiment were obtained. The results are shown in FIG. 10. The concentration of the keratan sulfate oligosaccharide in the figure means the final concentration.

The result reveals that the keratan sulfate tetrasaccharide (I) at concentrations of 0.01, 0.1 and 1.0 mg/ml remarkably inhibits the generation of active oxygen ($O_2^-$) depending upon the concentration, and this supports the existence of the anti-inflammatory function in the keratan sulfate tetrasaccharide (I). And also in the keratan sulfate disaccharide (III) and the keratan sulfate pentasaccharide (II), the inhibitory function for generation of active oxygen ($O_2^-$) was slightly observed. These results have suggested that the keratan sulfate oligosaccharide exerts an anti-inflammatory function by inhibiting the generation of active oxygen ($O_2$-) in neutrophile.

(Antiallergic function)

A variety of the keratan sulfate oligosaccharide was dropped in the eyes of the guinea pigs subjected to the induction of allergic conjunctivitis to examine the effect thereof.

(1) Effect of keratan sulfate tetrasaccharide (I) on allergic conjunctivitis

Figure 11:
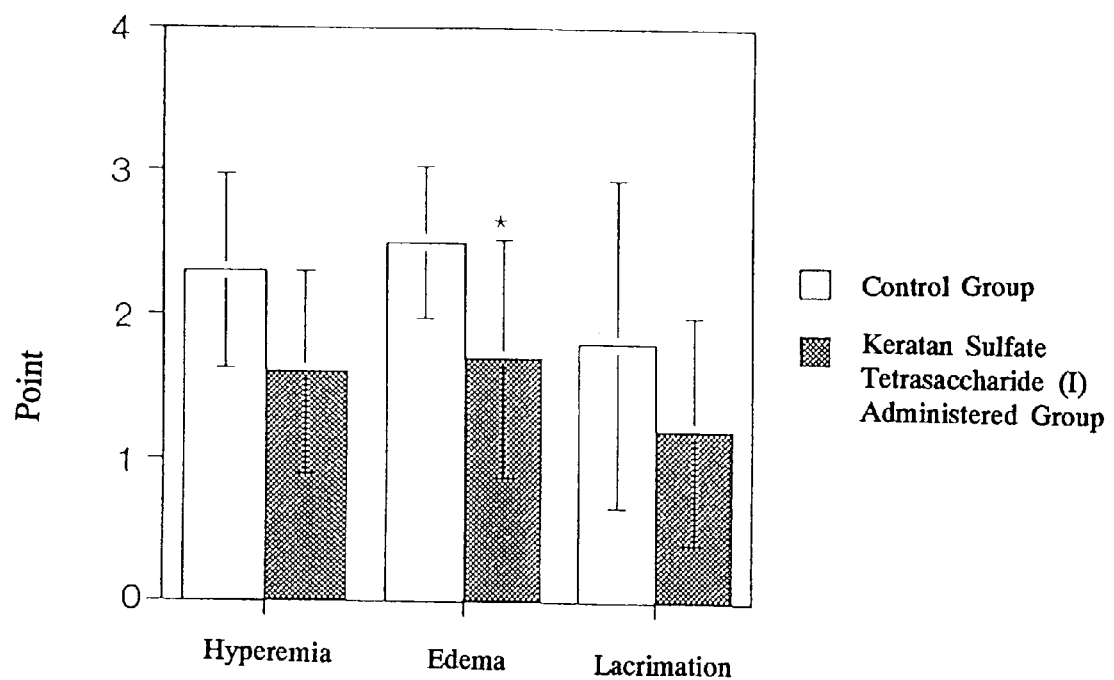
FIG. 11 is a graph showing the evaluation of the degree of conjunctivitis in the allergic conjunctivitis model guinea pigs subjected to administration of the keratan sulfate tetrasaccharide (I) or not.

Toluene diisocyanate (hereinafter referred to as TDI) was diluted with ethyl acetate to a concentration of 10%. To the bilateral vestibule of noses of 10 female Hartley guinea pigs of from about 900 to 1,000 g weight, the 10% TDI (10 μl/animal) obtained above was applied once a day for five days to prepare the TDI sensitization models. The PBS solution of the purified keratan sulfate tetrasaccharide (I) (100 mg/ml) which was prepared in Example 1 was dropped in the left eyes of the TDI sensitization models, while PBS was dropped in the right eyes as the control. The dose of dropping was one drop (48+4.6 μl (S.D.)) each from the eye dropper. After 10 minutes, 6.5 μl of 10% TDI was dropped to the both eyes to induce conjunctivitis. After five minutes standing, furthermore, the PBS solution of the keratan sulfate tetrasaccharide (I) (100 mg/ml) was dropped in the left eyes, and PBS was dropped in the right eyes. After 15 minutes, observation of the both eyes were carried out. The degree of conjunctivitis was evaluated regarding three items of hyperemia, edema and lacrimation into four grades such as point 0, +1, +2 and +3. As a result of this examination, the averages of the points and the standard deviations are shown in FIG. 11. In the figure, * represents that it has the significant difference with p<0.05 (wherein "p" means a level of significance by the $\chi^2$ test).

As a result, the keratan sulfate tetrasaccharide (I) tended to show inhibition in all the items of hyperemia, edema and lacrimation which were observed above, and especially, significantly inhibited edema compared with the control.

Figure 12:
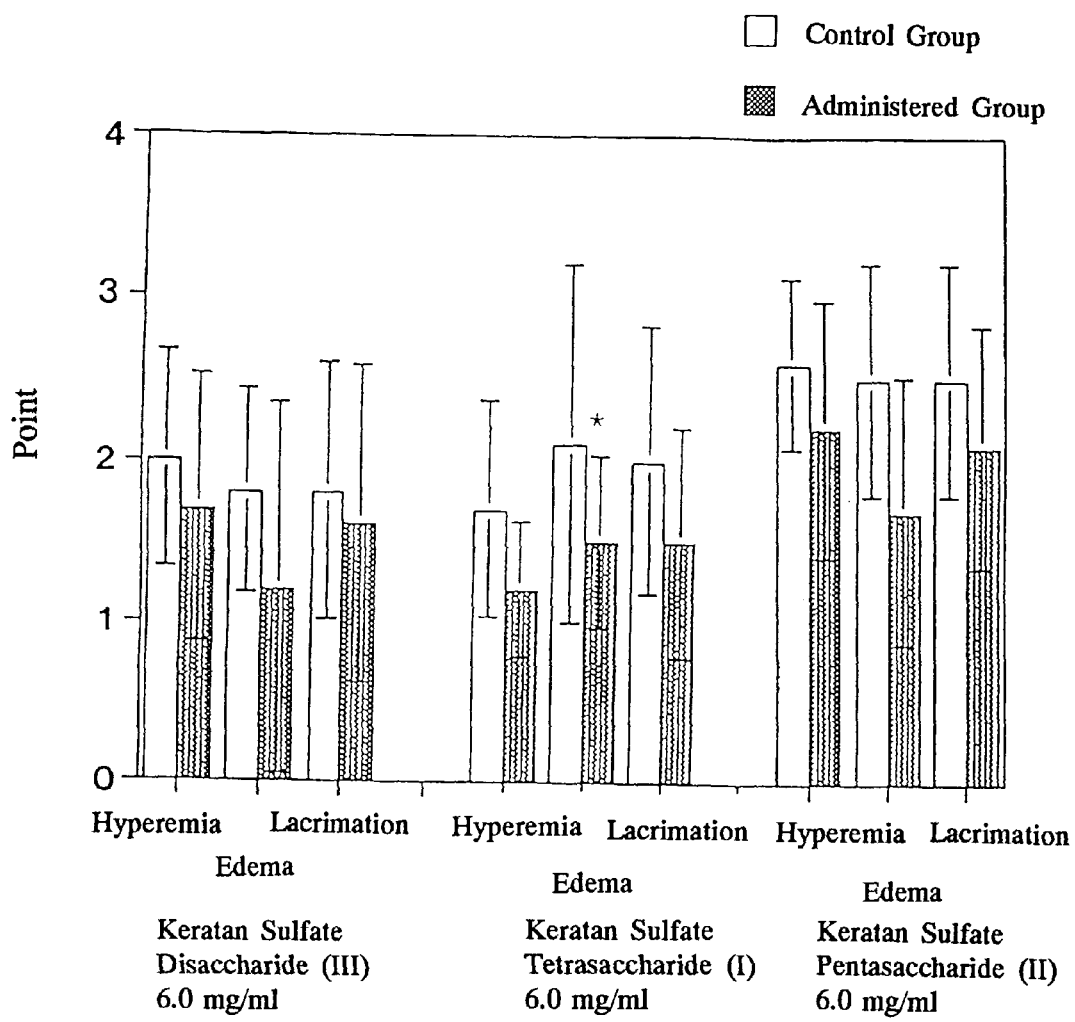
FIG. 12 is a graph showing the evaluation of the degree of conjunctivitis in the allergic conjunctivitis model guinea pigs subjected to administration of the keratan sulfate tetrasaccharide (I), the keratan sulfate pentasaccharide (II), or the keratan sulfate disaccharide (III), or not, respectively.

(2) Effect of varieties of keratan sulfate oligosaccharide on allergic conjunctivitis The PBS solution of the purified keratan sulfate disaccharide (III), the keratan sulfate tetrasaccharide (I), and the keratan sulfate pentasaccharide (II) (6.0 mg/ml, respectively) which were prepared in Example 1 described above as the test substances were dropped, respectively, in the left eyes of the TDI sensitization models of 10 animals a group each which were prepared in the same manner as in (1) described above, and PBS was dropped in the right eyes as the control. The degree of conjunctivitis was evaluated in the same manner as in (1) described above. As a result of this examination, the averages of the points and the standard deviations are shown in FIG. 12. In the figure, * represents that it has the significant difference with p<0.05 (wherein "p" means a level of significance by the $\chi^2$ test).

As a result, any one of the keratan sulfate disaccharide (III), the keratan sulfate tetrasaccharide (I), and the keratan sulfate pentasaccharide (II) tended to show inhibition in all the items of hyperemia, edema and lacrimation, and especially, it has been confirmed that the keratan sulfate tetrasaccharide (I) shows a significant inhibitory effect on edema.

Figure 13:
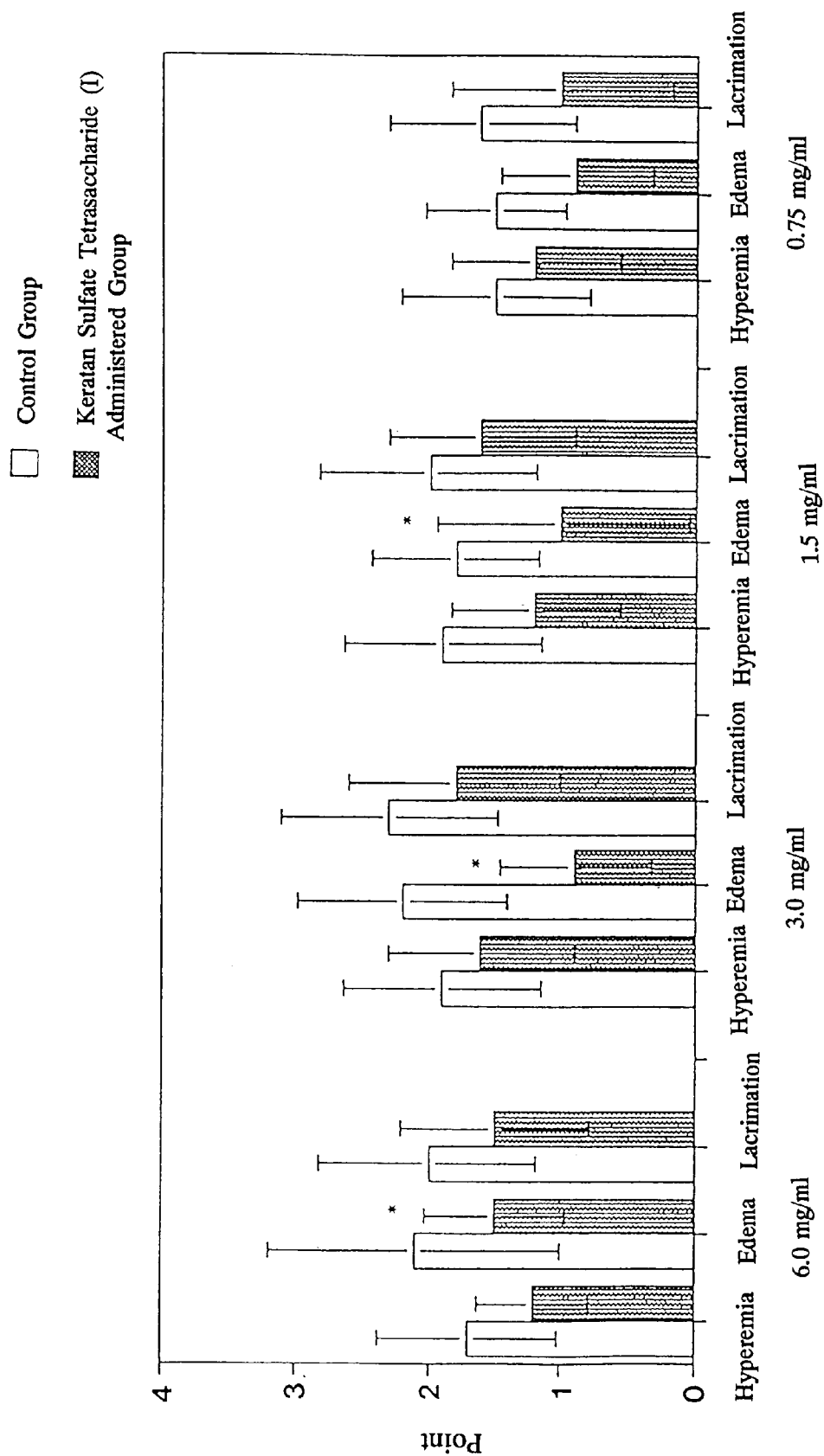
FIG. 13 is a graph showing the evaluation of the degree of conjunctivitis in the allergic conjunctivitis model guinea pigs subjected to administration of the keratan sulfate tetrasaccharide (I) in the various concentrations.

(3) Effect of keratan sulfate tetrasaccharide (I) at varieties of concentrations on allergic conjunctivitis The PBS solution containing the purified keratan sulfate tetrasaccharide (I) which was prepared in Example 1 described above, at varieties of concentrations (6 mg/ml, 3 mg/ml, 1.5 mg/ml or 0.75 mg/ml) as the test substance, were dropped, respectively, in the left eyes of the TDI sensitization models of 10 animals a group each which were prepared in the same manner as in (1) described above, and PBS was dropped in the right eyes as the control. The degree of conjunctivitis was evaluated in the same manner as in (1) described above. As a result of this examination, the averages of the points and the standard deviations are shown in FIG. 13. In the figure, * represents that it has the significant differnce with p<0.05 (wherein "p" means a level of signifcance by the $\chi^2$ test).

As a result, the PBS solutions of the keratan sulfate tetrasaccharide (I) at all the concentrations tended to show inhibition in all the items of hyperemia, edema and lacrimation, and especially, those at concentrations of 6 mg/ml, 3 mg/ml, and 1.5 mg/ml showed a significant inhibitory effect on edema.

<Immunomodulating function, cell differentiation inducing function, and apoptosis inducing function>

The effect of the keratan sulfate oligosaccharide was examined on MRL mice which are autoimmune disease model mice.

(1) Suppression effect on the weight of lymph node (1-1) Repeated intramuscular administration test of keratan sulfate tetrasaccharide (I) for four weeks in MRL mice The PBS solution of the purified keratan sulfate tetrasaccharide (I) (100 mg/ml) which was prepared in Example 1 described above at a dose of 10 mg/kg weight (hereinafter referred to as the administered group), and PBS as the control was intramuscularly injected, respectively, to the femoral region of MRL-lpr/lpr mice five times a week for four weeks. After that, the mice were subjected to anatomization, and the weight of spleens and mesenteric lymph nodes were determined to obtain the average weight. The results and the standard errors are shown in Table 11. In the table, "n" represents the number of mice used.

TABLE 11

| | Spleen Weight(mg) | Mesenteric Lymph Node Weight (mg) |
|---|---|---|
| Control Group (n = 8) | 1013 ± 233 | 1563 ± 352 |
| Administered Group (n = 9) | 704 ± 148 | 1338 ± 311 |

As a result, a suppressive tendency for the weight increase in spleens and mesenteric lymph nodes was observed in the group subjected to the injection of the keratan sulfate tetrasaccharide (I), and therefore, this has suggested the immunomodulating function of the keratan sulfate tetrasaccharide (I).

Figure 14:
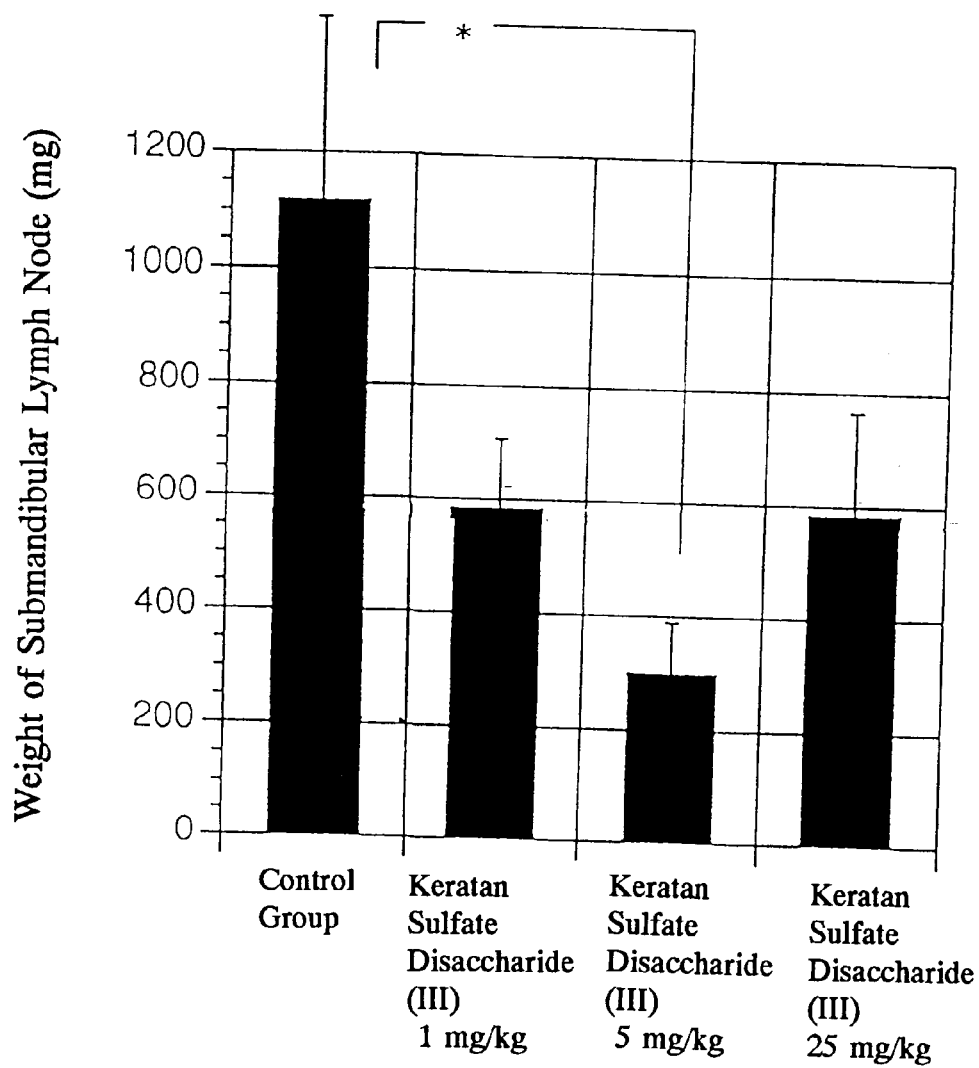
FIG. 14 is a graph showing the weight of submandibular lymph nodes of the MRL mice, which are autoimmune disease model mice, subjected to repeated administration of the various doses of the keratan sulfate disaccharide (III) for 28 days.

(1-2) Repeated intramuscular administration test of keratan sulfate disaccharide (III) for 28 days in MRL mice The PBS solution of the purified keratan sulfate disaccharide (III) which was prepared in Example 1 described above at a dose of 1 mg/kg, 5 mg/kg, or 25 mg/kg weight (hereinafter referred to as the 1 mg/kg administered group, the 5 mg/kg administered group, and the 25 mg/kg administered group, respectively), and PBS as the control (hereinafter sometimes referred to as the control group) was intramuscularly injected, respectively, to the femoral region of MRL-lpr/lpr mice seven times a week for four weeks. After that, the mice were subjected to anatomization, and the weight of submandibular lymph nodes was determined to obtain the average weight. The results and the standard errors are shown in FIG. 14. In each group, six mice were used. Further, in the figure, * represents that it has the significant difference with p<0.05 (wherein "p" means a level of significance by the Bonferroni multiple comparative test).

As a result, a suppressive effect on the weight increase in submandibular lymph nodes was observed in the keratan sulfate disaccharide (III) administered groups at any dose, especially in the 5 mg/kg administered group, a significant suppressive effect on the weight increase was observed compared with the control group, and therefore, these have suggested the immunomodulating function of the keratan sulfate disaccharide (III).

Figure 15:
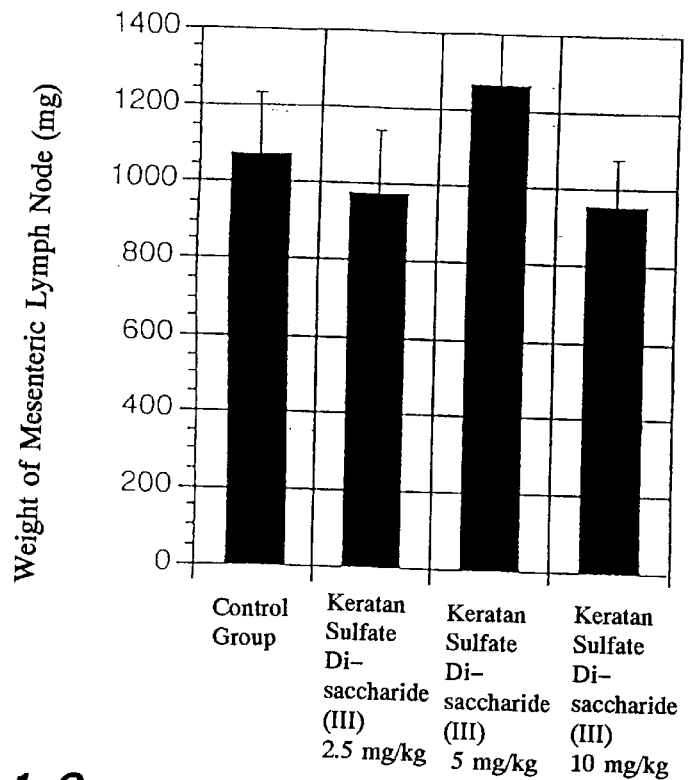
FIG. 15 is a graph showing the weight of mesenteric lymph nodes of the MRL mice subjected to repeated administration of the various doses of the keratan sulfate disaccharide (III) for 56 days.
Figure 16:
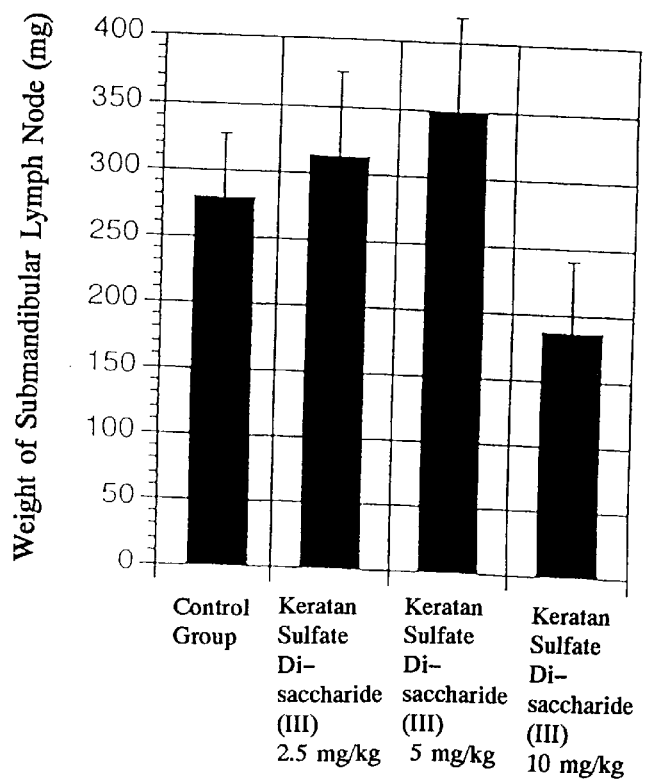
FIG. 16 is a graph showing the weight of submandibular lymph nodes of the MRL mice subjected to repeated administration of the various doses of the keratan sulfate disaccharide (III) for 56 days.

(1-3) Repeated intramuscular administration test of keratan sulfate disaccharide (III) for 56 days in MRL mice The PBS solution of the purified keratan sulfate disaccharide (III) which was prepared in Example 1 described above at a dose of 2.5 mg/kg, 5 mg/kg, or 10 mg/kg weight (hereinafter referred to as the 2.5 mg/kg administered group, the 5 mg/kg administered group, and the 10 mg/kg administered group, respectively), and PBS as the control (hereinafter sometimes referred to as the control group) was intramuscularly injected, respectively, to the femoral region of MRL-lpr/lpr mice seven times a week for eight weeks. After that, the mice were subjected to anatomization, and the weight of mesenteric lymph nodes and submandibular lymph nodes were determined to obtain the average weight, respectively. The results concerning mesenteric lymph nodes and submandibular lymph nodes are shown in FIG. 15 and FIG. 16 with the standard errors, respectively. In each group, seven mice were used.

Consequently, a suppressive effect on the weight increase in mesenteric lymph nodes was observed in the 2.5 mg/kg administered group of the keratan sulfate disaccharide (III), and that in mesenteric lymph nodes and submandibular lymph nodes were observed in the 10 mg/kg administered group, and therefore, these have suggested the immunomodulating function of the keratan sulfate disaccharide (III).

(2) Cell differentiation inducing function (2-1) Analysis of cell differentiation induction using cell staining concentration as an indicator The PBS solution of the purified keratan sulfate disaccharide (III) which was prepared in Example 1 described above at a dose of 1 mg/kg, 5 mg/kg, or 25 mg/kg weight (hereinafter referred to as the 1 mg/kg administered group, the 5 mg/kg administered group, and the 25 mg/kg administered group, respectively), and PBS as the control (hereinafter sometimes referred to as the control group) was intramuscularly injected, respectively, to the femoral region of MRL-lpr/lpr mice seven times a week for four weeks. After that, the mice were subjected to anatomization to prepare the section specimens (HE staining) of mesenteric lymph node and submandibular lymph node. The staining concentrations per unit area of the specimens were analyzed by an image analyzer (PIAS). In the undifferentiated cells, the staining concentration per unit area is low because proportion of the cytoplasm is high and the nuclei is stained thinly. In the differentiated cells, the staining concentration per unit area is high because proportion of the nuclei is high and it is stained thickly.

Figure 17:
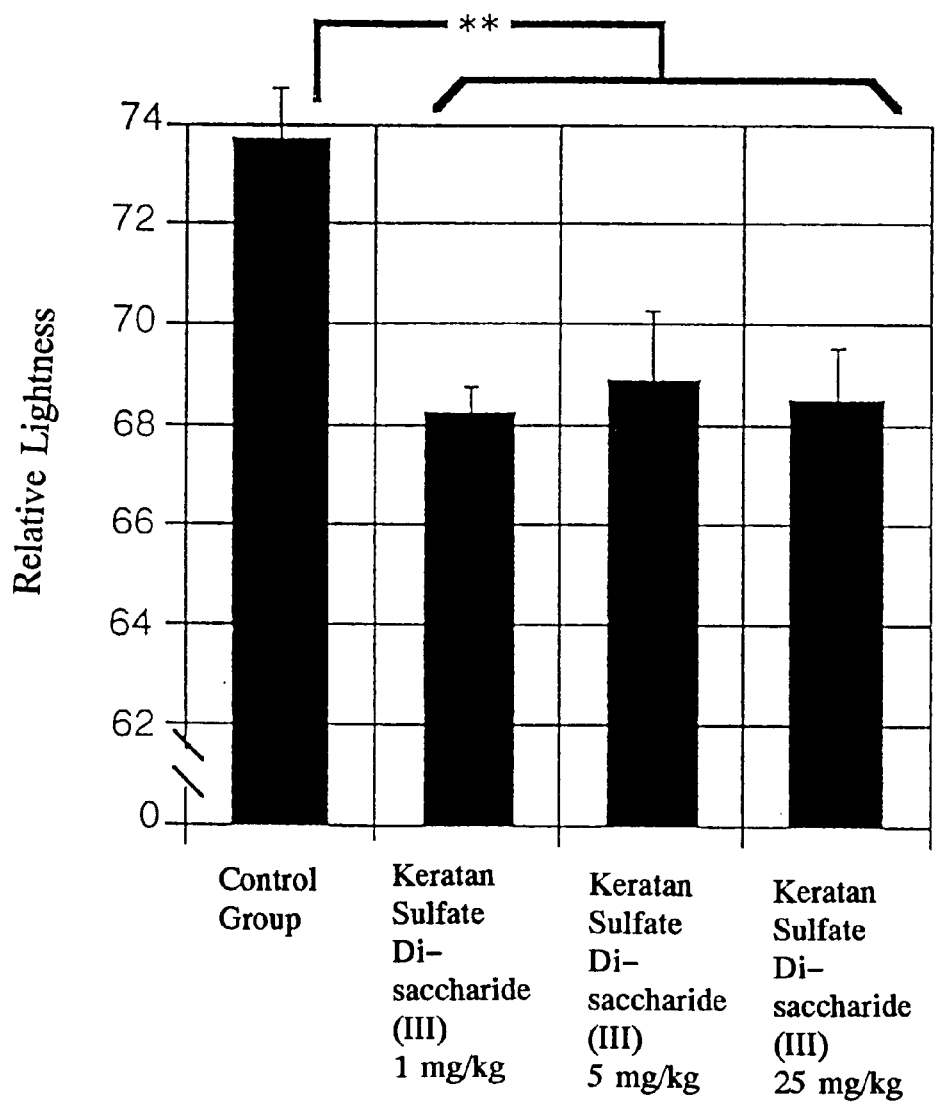
FIG. 17 is a graph showing the results of the analysis about staining concentrations of mesenteric lymph node section specimens (HE staining) of the MRL mice subjected to administration of the various doses of the keratan sulfate disaccharide (III).
Figure 18:
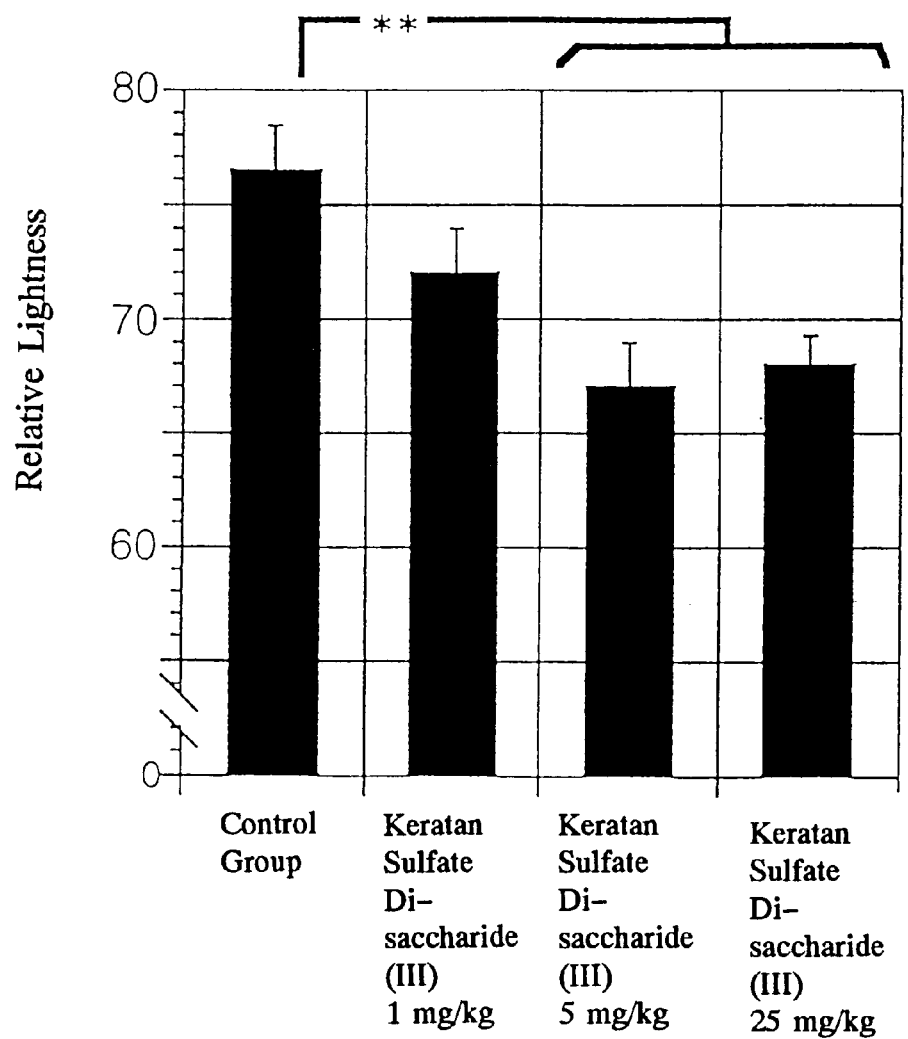
FIG. 18 is a graph showing the results of the analysis about staining concentrations of submandibular lymph node section specimens (HE staining) of the MRL mice subjected to administration of the various doses of the keratan sulfate disaccharide (III).

The results of the analysis of mesenteric lymph nodes and submandibular lymph nodes are shown in FIG. 17 and FIG. 18 with the standard errors, respectively. In the figures, ** represents that it has the significant difference with $p<0.01$ (wherein "p" means a level of significance by the Bonferroni multiple comparative test). In each group, six mice were used.

Consequently, an increase in the staining concentration per unit area (decrease in relative lightness) was observed in the keratan sulfate disaccharide (II) administered groups at any dose, and especially in the 5 mg/kg administered group and the 25 mg/kg administered group, the staining concentrations increased significantly compared with the control group. These indicate an increase in the differentiated cells by the keratan sulfate disaccharide (III), and have suggested the cell differentiation inducing function of the keratan sulfate disaccharide (III).

(2-2) Analysis of cell differentiation induction using lymphocyte surface antigen of lymph node as an indicator The PBS solution of the purified keratan sulfate disaccharide (III) which was prepared in Example 1 described above at a dose of 2.5 mg/kg, 5 mg/kg, or 10 mg/kg weight (hereinafter referred to as the 2.5 mg/kg administered group, the 5 mg/kg administered group, and the 10 mg/kg administered group, respectively), and PBS as the control (hereinafter sometimes referred to as the control group) was intramuscularly injected, respectively, to the femoral region of MRL-lpr/lpr mice seven times a week for eight weeks. After that, the mice were subjected to anatomization, and the lymph nodes were minced on a cell strainer (Falcon 2350) to prepare the lymphocyte. The lymphocyte prepared of each group was subjected to the double immune staining with the anti-CD3 antibody (Seikagaku Corporation) and the anti-CD4 antibody (Pharminjen), that with the anti-CD3 antibody and the anti-CD8a antibody (Pharminjen), and that with the anti-CD3 antibody and the anti-B220 antibody (Pharminjen), respectively. The CD3, CD4, and CDBa are cell surface antigens which are expressed on T cells, and the B220 is that expressed on B cells. And it is known that no expression of these cell surface antigens is observed on null lymphocytes.

Figure 19:
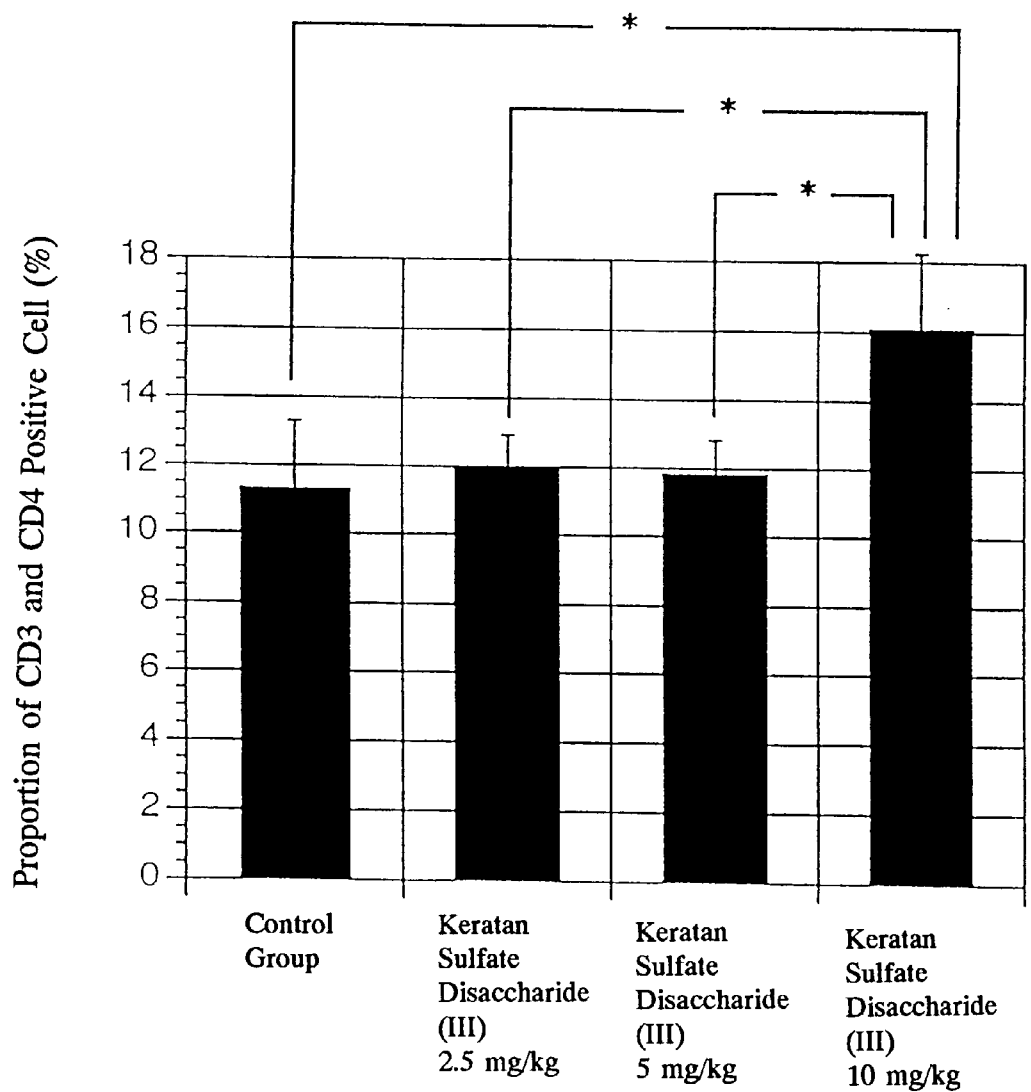
FIG. 19 is a graph showing the proportions (%) of the CD3 and CD4 positive cells to lymphocytes of the MRL mice subjected to administration of the various doses of the keratan sulfate disaccharide (III).
Figure 20:
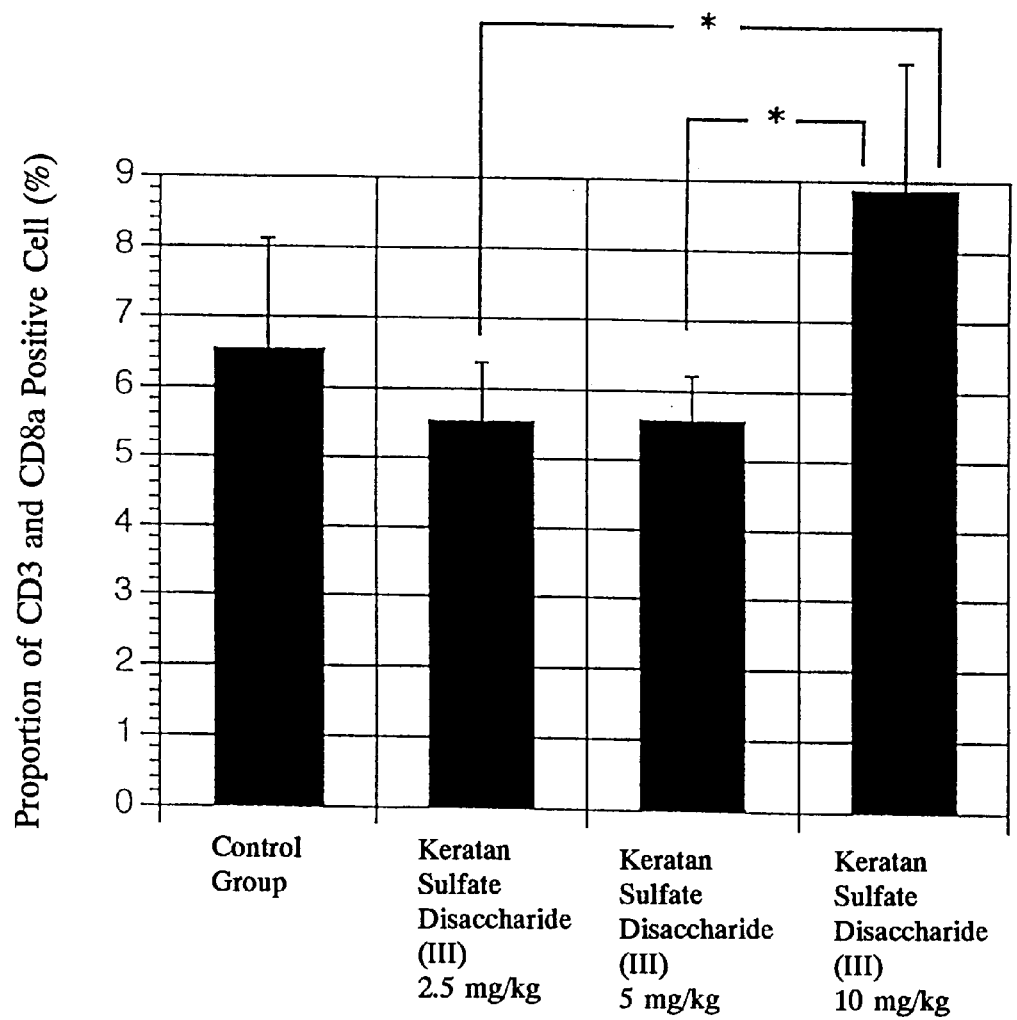
FIG. 20 is a graph showing the proportions (%) of the CD3 and CD8a positive cells to lymphocytes of the MRL mice subjected to administration of the various doses of the keratan sulfate disaccharide (III).
Figure 21:
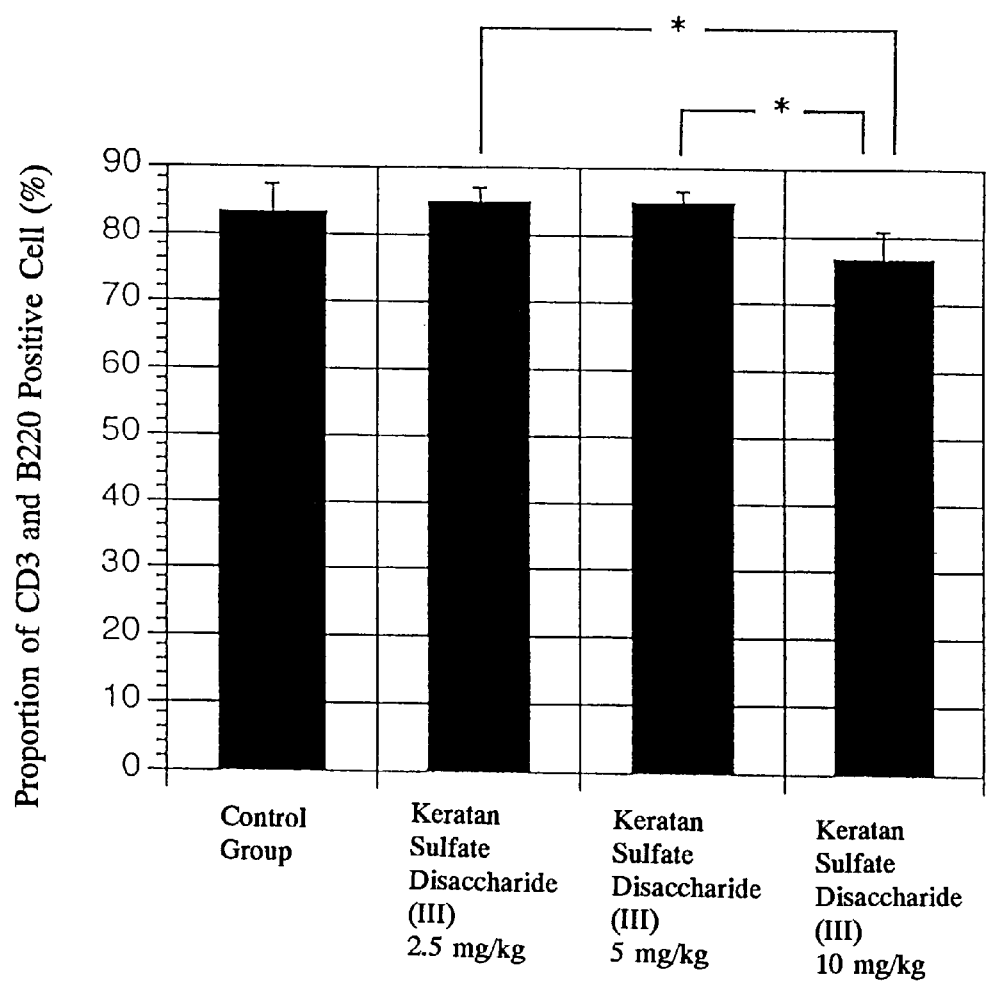
FIG. 21 is a graph showing the proportions (%) of the CD3 and B220 positive cells to lymphocytes of the MRL mice subjected to administration of the various doses of the keratan sulfate disaccharide (III).

The proportion (%) of the CD3 and CD4 positive cells (hereinafter sometimes referred to as "the CD3+CD4+ cells"; mainly helper T cells) to all the lymphocytes and the standard errors are shown in FIG. 19, that of the CD3 and CD8a positive cells (hereinafter sometimes referred to as "the CD3+CD8a+cells"; mainly suppressor T cells and cytotoxic T cells) and the standard errors are shown in FIG. 20, and that of the CD3 and B220 positive cells (hereinafter sometimes referred to as "the CD3+B220+cells"; abnormal T cells having the surface antigens of B cells) and the standard errors are shown in FIG. 21. In the figures, * represents that it has the significant difference with $p<0.05$ (wherein "p" means a level of significance by the Ryan multiple comparative test). In each group, seven mice were used.

As apparent from FIG. 19, the CD3+CD4+ cells in the 10 mg/kg administered group of the keratan sulfate disaccharide (III) increased significantly to that in the control group, the 2.5 mg/kg administered group, and the 5 mg/kg administered group. This indicates the differentiation of the null lymphocytes into the CD3+CD4+ cells by administration of an adequate amount of the keratan sulfate disaccharide (III).

As apparent from FIG. 20, the CD3+CD8a+ cells in the 10 mg/kg administered group of the keratan sulfate disaccharide (III) increased to that in the control group, the 2.5 mg/kg administered group, and the 5 mg/kg administered group. This indicates the differentiation of the null lymphocytes into the CD3+CD8a+ cells by administration of an adequate amount of the keratan sulfate disaccharide (III).

As apparent from FIG. 21, the CD3+B220+ cells in the 10 mg/kg administered group of the keratan sulfate disaccharide (III) decreased to that in the control group, the 2.5 mg/kg administered group, and the 5 mg/kg administered group. This indicates a decrease of the CD3+B220+ cells which are abnormal ones by administration of an adequate amount of the keratan sulfate disaccharide (III), and supports the differentiation induction into normal lymphocytes by that.

These results have suggested the cell differentiation inducing function of the keratan sulfate disaccharide (III).

(3) Apoptosis inducing function

Figure 22:
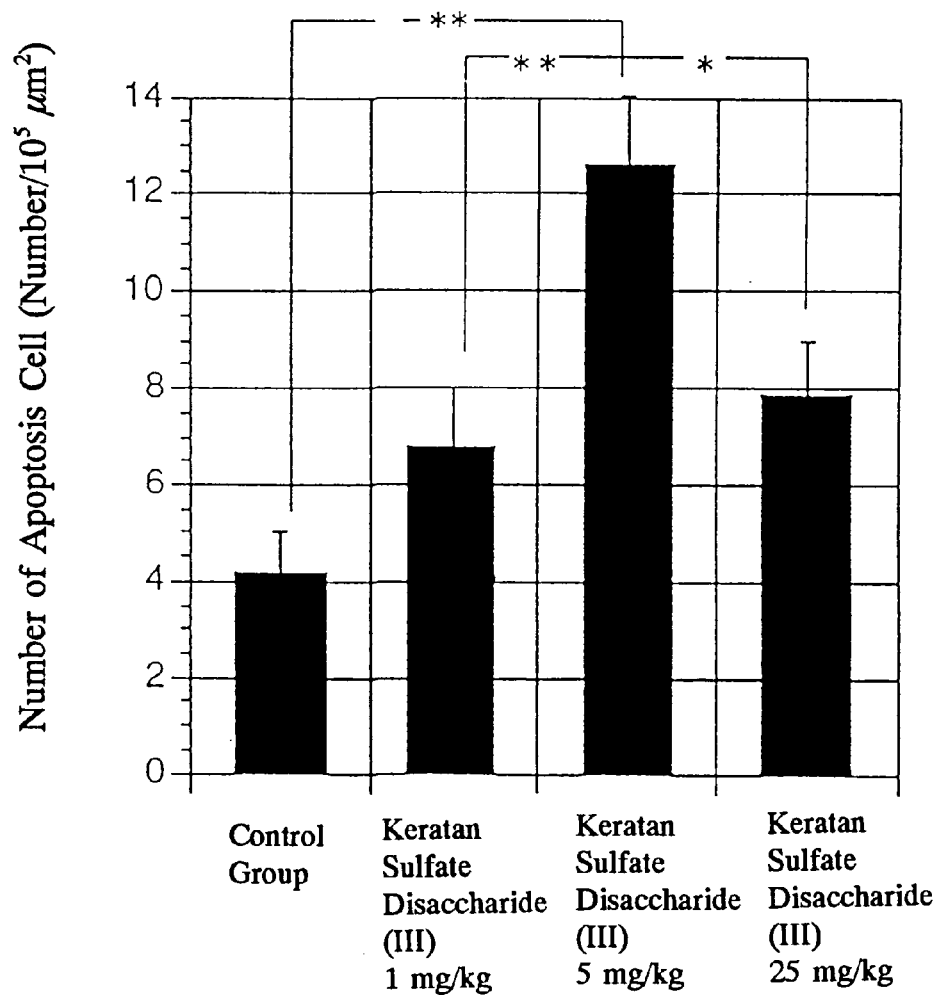
FIG. 22 is a graph showing the number of apoptosis cells in submandibular lymph nodes of the MRL mice subjected to administration of the various doses of the keratan sulfate disaccharide (III).

The PBS solution of the purified keratan sulfate disaccharide (III) which was prepared in Example 1 described above at a dose of 1 mg/kg, 5 mg/kg, or 25 mg/kg weight (hereinafter referred to as the 1 mg/kg administered group, the 5 mg/kg administered group, and the 25 mg/kg administered group, respectively), and PBS as the control (hereinafter sometimes referred to as the control group) was intramuscularly injected, respectively, to the femoral region of MRL-lpr/lpr mice seven times a week for four weeks. After that, the mice were subjected to anatomization to prepare the section specimens of submandibular lymph node (stained by the method of Gavrieli et al.; Terminal deoxynucleotidyl transferase (TdT)—mediated nick end labeling method; (J. Cell Biol., 119, 493–501 (1992))). In this staining method, apoptosis induced cells can be detected by detecting fragmented DNA ends. The specimens prepared was observed by a light microscope to determine the number of stained cells (the apoptosis induced cells; hereinafter sometimes referred to as the apoptosis cells) per unit area. The results and the standard errors are shown in FIG. 22. In the figure, * and ** represent that they have the significant difference with $p<0.05$ and $p<0.01$, respectively (wherein "p" means a level of significance by the Bonferroni multiple comparative test). In each group, six mice were used.

Consequently, an increase in the number of the apoptosis cells was observed in the keratan sulfate disaccharide (III) administered groups at any dose, and especially in the 5 mg/kg administered group, the number of the apoptosis cells increased significantly to the control group.

Also, the section specimens (HE staining) of submandibular lymph node of the mice in each group were prepared to observe the existence of the apoptic body by the light microscope. As a result, the scattering of the apoptic body was observed in the keratan sulfate disaccharide (III) administered groups at any dose.

These results have suggested the apoptosis inducing function of the keratan sulfate disaccharide (III).

From the results described above, the immunomodulating function, cell differentiation inducing function, and apoptosis inducing function of the keratan sulfate bligosaccharide were confirmed.

EXAMPLE 3 Ointment

Following a conventional method, the purified keratan sulfate tetrasaccharide (I) prepared in Example 1 was dissolved in a hydrophilic ointment of the Japanese Pharmacopoeia at a concentration of 10 mg/ml to prepare an ointment. This ointment can be used both as an anti-inflammatory agent and antiallergic agent.

EXAMPLE 4 Eye Drop

Following a conventional method, the purified keratan sulfate tetrasaccharide (I) prepared in Example 1 and sodium hyaluronate were dissolved in the saline adjusted to pH from 6.8 to 7.6 with phosphate at concentrations of 10 mg/ml and 2 mg/ml, respectively, to prepare an eye drop. This eye drop can be used both as anti-inflammatory agent and antiallergic agent.

EXAMPLE 5 Liposome Inclusion

The purified keratan sulfate tetrasaccharide (I) prepared in Example 1 was dissolved at concentration of 10 mg/ml in a liposome inclusion (Aquasome LA; Nikko Chemicals) containing lecithin and subjected to ultrasonication for clathration. This liposome inclusion can be used as any agent of an anti-inflammatory agent, antiallergic agent, immunomodulator, cell differentiation inducer, and apoptosis inducer.

EXAMPLE 6 Injection

Following a conventional method, the purified keratan sulfate tetrasaccharide (I) prepared in Example 1 was dissolved in the saline adjusted to pH from 6.8 to 7.6 with phosphate at a concentration of 10 mg/ml and the solution was filtered asepticly with 0.22 μm filter to prepare an injection. This injection can be used as any agent of an anti-inflammatory agent, antiallergic agent, immunomodulator, cell differentiation inducer, and apoptosis inducer.

INDUSTRIAL APPLICABILITY

The purified high-sulfated keratan sulfate oligosaccharide fraction of the present invention has an extremely high extent of purification and does not substantially contain endotoxin, nucleic acid, protein, protease, and other glycosaminoglycans except for the oligosaccharide described above, and therefore, it can be used as pharmaceuticals such as a novel anti-inflammatory agent.

What is claimed is:

1. A pharmaceutical composition comprising at least either high-sulfated keratan sulfate oligosaccharide or pharmaceutically acceptable salt thereof, and pharmaceutically acceptable carrier, said high-sulfated keratan sulfate oligosaccharide comprising no fucose and represented Gal(6S)β1→4GlcNAc(6S)

wherein Gal represents a galactose, GlcN represents a glucosamine, Ac represents an acetyl group, and 6S represents a 6-O-sulfate ester.

2. The pharmaceutical composition as claimed in claim 1, wherein said high-sulfated keratan sulfate oligosaccharide is included in a high-sulfated keratan sulfate oligosaccharidefraction, as a main component, which is obtained by degrading high-sulfated keratan sulfate derived from cartilaginous fishes with a keratan sulfate-degrading enzyme of endo-β-N-acetylglucosaminidase type and then fractionating the degradation products.

3. The pharmaceutical composition as claimed in claim 2, wherein said keratan sulfate-degrading enzyme of endo-β-N-acetylglucosaminidase type is a keratan sulfate-degrading enzyme having the following physical and chemical properties:

1) action:
   the degrading enzyme acts on keratan sulfate and hydrolyses the N-acetylglucosaminidic linkage thereof;

2) substrate specificity:
   the degrading enzyme acts on keratan sulfate I, keratan sulfate II, and keratan polysulfate and produces sulfated keratan sulfate disaccharide and sulfated keratan sulfate tetrasaccharide as main degradation products;

3) optimum reaction pH:
   the degrading enzyme has an optimum reaction pH of from 4.5 to 6 in the 0.1 M acetate buffer or 10 mM tris-acetate buffer at 37° C.;

4) pH stability: the degrading enzyme has a pH stability of from 6 to 7 when the degrading enzyme is stood in the 0.1 M acetate buffer or 10 mM tris-acetate buffer at 37° C. for an hour;

5) optimum reaction temperature:
   the degrading enzyme has an optimum reaction temperature of from 50° C. to 60° C. when the degrading enzyme reacts in the 0.1 M acetate buffer, pH 6.0, for 10 minutes; and 6) thermostability:
   the degrading enzyme is at least stable at 45° C. or less when the degrading enzyme is stood in the 0.1 M acetate buffer, pH 6.0, for an hour.

4. A pharmaceutical composition comprising at least either high sulfated keratan sulfate oligosaccharide or pharmaceutically acceptable salt thereof, and pharmaceutically acceptable carrier, said high-sulfated keratan sulfate oligosaccharide containing no fucose and being selected from the group consisting of tetrasulfated N-acetyllactosamine tetrasaccharide represented by the formula (I), trisulfated N-acetyllactosamine pentasaccharide represented by the formula (II), and disulfated N-acetyllactosamine disaccharide represented by the formula (III):

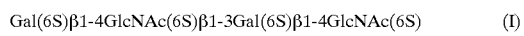

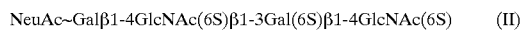

wherein Gal represents a galactose, GlcN represents a glucosamine, Neu represents a neuraminic acid, Ac represents an acetyl group, 6S represents a 6-O-sulfate ester, and ~ represents an α2,3 bond or α2,6 bond.

5. The pharmaceutical composition as claimed in claim 4, wherein said high-sulfated keratan sulfate oligosaccharide is included in high-sulfated keratan sulfate oligosaccharidefraction, as a main component, which is obtained by degrading high-sulfated keratan sulfate derived from cartilaginous fishes with a keratan sulfate-degrading enzyme of endo-β-N-acetylglucosaminidase type and then fractionating the degradation products.

6. The pharmaceutical composition as claimed in claim 5, wherein said keratan sulfate-degrading enzyme of endo-β-N-acetylglucosaminidase type is a keratan sulfate-degrading enzyme having the following physical and chemical properties:

1) action:
   the degrading enzyme acts on keratan sulfate and hydrolyses the N-acetylglucosaminidic linkage thereof;
2) substrate specificity:
   the degrading enzyme acts on keratan sulfate I, keratan sulfate II, and keratan polysulfate and produces sulfated keratan sulfate disaccharide and sulfated keratan sulfate tetrasaccharide as main degradation products;
3) optimum reaction pH:
   the degrading enzyme has an optimum reaction pH of from 4.5 to 6 in the 0.1 M acetate buffer or 10 mM tris-acetate buffer at 37° C.;
4) pH stability:
   the degrading enzyme has a pH stability of from 6 to 7 when the degrading enzyme is stood in the 0.1 M acetate buffer or 10 mM tris-acetate buffer at 37° C. for an hour;
5) optimum reaction temperature:
   the degrading enzyme has an optimum reaction temperature of from 50° C. to 60° C. when the degrading enzyme reacts in the 0.1 M acetate buffer, pH 6.0, for 10 minutes; and
6) thermostability:
   the degrading enzyme is at least stable at 45° C. or less when the degrading enzyme is stood in the 0.1 M acetate buffer, pH 6.0, for an hour.

7. A method for producing a high-sulfated keratan sulfate oligosaccharide, comprising the steps of degrading high-sulfated keratan sulfate with a keratan sulfate-degrading enzyme having the following physical and chemical properties:

(1) action:
   the degrading enzyme acts on keratan sulfate and hydrolyses the N-acetylglucosaminidic linkage thereof;
(2) substrate specificity:
   the degrading enzyme acts on keratan sulfate 1, keratan sulfate 11, and keratan polysulfate and produces sulfated keratan sulfate disaccharide and sulfated keratan sulfate tetrasaccharide as main degradation products;

(3) optimum reaction pH:
   the degrading enzyme has an optimum reaction pH of from 4.5 to 6 in the 0.1 M acetate buffer or 10 mM tris-acetate buffer at 37° C.;
(4) pH stability:
   the degrading enzyme has a pH stability of from 6 to 7 when the degrading enzyme is stood in the 0.1 M acetate buffer or 10 mM tris-acetate buffer at 37° C. for an hour;
(5) optimum reaction temperature:
   the degrading enzyme has an optimum reaction temperature of from 50° C. to 60° C. when the degrading enzyme reacts in the 0.1 M acetate buffer, pH 6.0, for 10 minutes; and
(6) thermostability:
   the degrading enzyme is at least stable at 45° C. or less when the degrading enzyme is stood in the 0.1 M acetate buffer, pH 6.0, for an hour;
   and fractionating a high-sulfated keratan sulfate oligosaccharide from the degradation products, said high-sulfated keratan sulfate oligosaccharide comprising no fucose and, as a constitutional ingredient, at least disaccharide represented by the following formula:

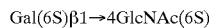

Gal(6S)β1→4GlcNAc(6S)

wherein Gal represents a galactose. GlcN represents a glucosamine, Ac represents an acetyl group and 6S represents a 6-O-sulfate ester.

8. The method for producing a high-sulfated keratan sulfate oligosaccharide as claimed in claim 7, wherein said high-sulfated keratan sulfate is high-sulfated keratan sulfate derived from cartilaginous fishes.

9. The method for producing a high-sulfated keratan sulfate oligosaccharide as claimed in claim 7, wherein the high-sulfated keratan sulfate oligosaccharide is selected from the group consisting of tetrasulfated N-acetyllactosamine tetrasaccharide represented by the formula (I); trisulfated N-acetyllactosamine pentasaccharide represented by the formula (II), and disulfated N-acetyllactosamine disaccharide represented by the formula (III):

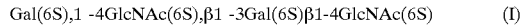

Gal(6S),1 -4GlcNAc(6S),β1 -3Gal(6S)β1-4GlcNAc(6S)    (I)

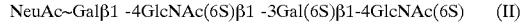

NeuAc~Galβ1 -4GlcNAc(6S)β1 -3Gal(6S)β1-4GlcNAc(6S)    (II)

Gal(6S)β1-4GlcNAc(6S)    (III)

wherein Gal represents a galactose, GlcN represents a glucosamine, Neu represents a neuraminic acid, Ac represents an acetyl group, 6S represents a 6-O-sulfate ester, and ~ represents an α2, 3 bond or α2, 6 bond.

* * * * *

UNITED STATES PATENT AND TRADEMARK OFFICE
CERTIFICATE OF CORRECTION

PATENT NO. : 5,939,403
DATED : August 17, 1999
INVENTOR(S) : Hiroshi Maruyama et al.

It is certified that error appears in the above-indentified patent and that said Letters Patent is hereby corrected as shown below:

Column 4/line 63, delete "endo-p-N-acetylglucosaminidase" and insert --endo-β-N-acetylglucosaminidase--;
Column 5/line 15, delete "1 pmol" and insert --1 μmol--;
Column 8/line 67, delete "apoptosis Inducer" and insert --poptosis inducer--;
Column 14/line 15, delete "8 (ppm)" and insert --δ (ppm)--;
Column 14/line 21, delete "4.402(1H, d), and insert --4.402(1H, dd)--;
Column 14/line 31, delete "³C-NMR" and insert --$^{13}$C-NMR--;
Column 24/line 52, delete "(48+4.6μl(S.D.))" and insert --(48±4.6μl(S.D.));
Column 29/line 9, delete "bligosaccharide" and insert --oligosaccharide--'
Column 29/line 65, add --by the following formula:-- after represented;

UNITED STATES PATENT AND TRADEMARK OFFICE
CERTIFICATE OF CORRECTION

PATENT NO. : 5,939,403
DATED : August 17,, 1999
INVENTOR(S) : Hiroshi Maruyama, et al.

It is certified that error appears in the above-indentified patent and that said Letters Patent is hereby corrected as shown below:

Column 30/line 7, delete "oligosaccharidefraction" and insert --oligosaccharide fraction--;
Column 30/line 19, delete "hydrolyses" and insert --hydrolyzes--;
Column 31/line 1, delete "oligosaccharidefraction and insert --oligosaccharide fraction--;
Column 31/line 13, delete "hydrolyses" and insert --hydrolyzes--'
Column 31/line 51, delete "karatan sulfate 1" and insert --keratan sulfate I--;
Column 31/line 51, delete "sulfate 11" and insert --sulfate II--;
Column 32/line 23-24, delete ", as a constitutional ingredient, at least disaccharide";
Column 32/line 45, delete "Gal(6S),1-4GlcNAc(6S),β1-3Gal(6S)β1-4GlcNAc(6S)"
    and insert -- Gal(6S)β1-4GlcNAc(6S)β1-3Gal(6S)β1-4GlcNAc(6S)--.

Signed and Sealed this

Twentieth Day of March, 2001

Attest:

NICHOLAS P. GODICI

Attesting Officer        Acting Director of the United States Patent and Trademark Office

UNITED STATES PATENT AND TRADEMARK OFFICE
CERTIFICATE OF CORRECTION

PATENT NO. : 5,939,403
DATED : August 17, 1999
INVENTOR(S) : Hiroshi Maruyama, et al.

It is certified that error appears in the above-identified patent and that said Letters Patent is hereby corrected as shown below:

Column 8,
Line 67, delete "apoptosis Inducer" and insert -- apoptosis inducer --;

Column 14,
Line 46, delete "$^3$C-NMR" and isnert -- $^{13}$C-NMR --;

Column 31,
Line 52, delete "keratan sulfate 11 and insert -- keratan sulfate II --.

Signed and Sealed this

Fourth Day of December, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.    : 5,939,403
DATED         : August 17, 1999
INVENTOR(S)   : Hiroshi Maruyama et al.

It is certified that error appears in the above-identified patent and that said Letters Patent is hereby corrected as shown below:

Column 4,
Line 63, delete "endo-p-N-acetylglucosaminidase" and insert
-- endo-β-N-acetylglucosaminidase --;

Column 5,
Line 15, delete "1 pmol" and insert -- 1 μmol --;

Column 8,
Line 67, delete "apoptosis Inducer" and insert -- poptosis inducer --;

Column 14,
Line 15, delete "8 (ppm)" and insert -- δ (ppm) --;
Line 21, delete "4.402(1H, d)," and insert -- 4.402(1H, dd) --;
Line 31, delete "$^3$C-NMR" and insert -- $^{13}$C-NMR --;

Column 24,
Line 52, delete "(48+4.6μ1(S.D.))" and insert -- (48±4.6μ1(S.D.)) --;

Column 29,
Line 9, delete "bligosaccharide" and insert -- oligosaccharide --;
Line 65, add -- by the following formula: -- after "represented";

Column 30,
Line 7, delete "oligosaccharidefraction" and insert -- oligosaccharide fraction --;
Line 19, delete "hydrolyses" and insert -- hydrolyzes --;

Column 31,
Line 1, delete "oligosaccharidefraction" and insert -- oligosaccharide fraction --;
Line 13, delete "hydrolyses" and insert -- hydrolyzes --;
Line 51, delete "karatan sulfate 1" and insert -- keratan sulfate I --;
Line 51, delete "sulfate 11" and insert -- sulfate II --;

UNITED STATES PATENT AND TRADEMARK OFFICE
CERTIFICATE OF CORRECTION

PATENT NO. : 5,939,403
DATED : August 17, 1999
INVENTOR(S) : Hiroshi Maruyama et al.

It is certified that error appears in the above-identified patent and that said Letters Patent is hereby corrected as shown below:

<u>Column 32,</u>
Lines 23-24, delete ", as a constitutional ingredient, at least disaccharide";
Line 45, delete "Gal(6S),1-4GlcNAc(6S),β1-3Gal(6S)β1-4GlcNAc(6S)"
and insert -- Gal(6S)β1-4GlcNAc(6S)β1-3Gal(6S)β1-4GlcNAc(6S) --.

Signed and Sealed this

Eleventh Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 5,939,403
DATED : August 17, 1999
INVENTOR(S) : Hiroshi Maruyama et al.

It is certified that error appears in the above-identified patent and that said Letters Patent is hereby corrected as shown below:

Column 4,
Line 63, delete "endo-p-N-acetylglucosaminidase" and insert
-- endo-β-N-acetylglucosaminidase --;

Column 5,
Line 15, delete "1 pmol" and insert -- 1 μmol --;

Column 8,
Line 67, delete "apoptosis Inducer" and insert -- poptosis inducer --;

Column 14,
Line 15, delete "8 (ppm)" and insert -- δ (ppm) --;
Line 21, delete "4.402(1H, d)," and insert -- 4.402(1H, dd) --;
Line 31, delete "$^3$C-NMR" and insert -- $^{13}$C-NMR --;

Column 24,
Line 52, delete "(48+4.6μ1(S.D.))" and insert -- (48±4.6μ1(S.D.)) --;

Column 29,
Line 9, delete "bligosaccharide" and insert -- oligosaccharide --;
Line 65, add -- by the following formula: -- after "represented";

Column 30,
Line 7, delete "oligosaccharidefraction" and insert -- oligosaccharide fraction --;
Line 19, delete "hydrolyses" and insert -- hydrolyzes --;

Column 31,
Line 1, delete "oligosaccharidefraction" and insert -- oligosaccharide fraction --;
Line 13, delete "hydrolyses" and insert -- hydrolyzes --;
Line 51, delete "karatan sulfate 1" and insert -- keratan sulfate I --;
Line 51, delete "sulfate 11" and insert -- sulfate II --;

UNITED STATES PATENT AND TRADEMARK OFFICE
CERTIFICATE OF CORRECTION

PATENT NO.   : 5,939,403
DATED        : August 17, 1999
INVENTOR(S)  : Hiroshi Maruyama et al.

It is certified that error appears in the above-identified patent and that said Letters Patent is hereby corrected as shown below:

Column 32,
Lines 23-24, delete ", as a constitutional ingredient, at least disaccharide";
Line 45, delete "Gal(6S),1-4GlcNAc(6S),β1-3Gal(6S)β1-4GlcNAc(6S)" and insert -- Gal(6S)β1-4GlcNAc(6S)β1-3Gal(6S)β1-4GlcNAc(6S) --.

Signed and Sealed this

Eighteenth Day of February, 2003

JAMES E. ROGAN
*Director of the United States Patent and Trademark Office*